(12) United States Patent
Sriram et al.

(10) Patent No.: US 11,634,437 B2
(45) Date of Patent: Apr. 25, 2023

(54) FLUORESCENT COMPOUNDS SPECIFIC FOR PLURIPOTENT STEM CELLS AND REPROGRAMMING-READY CELLS AND METHODS OF USING THE SAME

(71) Applicant: Agency for Science, Technology and Research, Singapore (SG)

(72) Inventors: Sandhya Sriram, Singapore (SG); Shigeki Sugii, Singapore (SG); Young Tae Chang, Singapore (SG); Nam-Young Kang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 149 days.

(21) Appl. No.: 16/620,792

(22) PCT Filed: Jul. 4, 2018

(86) PCT No.: PCT/SG2018/050329
§ 371 (c)(1),
(2) Date: Dec. 9, 2019

(87) PCT Pub. No.: WO2019/009810
PCT Pub. Date: Jan. 10, 2019

(65) Prior Publication Data
US 2020/0123179 A1  Apr. 23, 2020

(30) Foreign Application Priority Data

Jul. 4, 2017 (SG) .......................... 10201705493P

(51) Int. Cl.
*G01N 33/58* (2006.01)
*C12N 5/0735* (2010.01)
(Continued)

(52) U.S. Cl.
CPC ............ *C07F 5/022* (2013.01); *C12N 5/0606* (2013.01); *C12N 5/0696* (2013.01); *G01N 33/582* (2013.01)

(58) Field of Classification Search
CPC ........ G01N 33/582; C09B 57/00; C07F 5/022
See application file for complete search history.

(56) References Cited

U.S. PATENT DOCUMENTS

| 8,735,150 | B2 | 5/2014 | Chang et al. |
| 9,423,395 | B2 | 8/2016 | Chang et al. |
| 10,416,153 | B2 * | 9/2019 | Chang ................ A61K 49/0021 |

FOREIGN PATENT DOCUMENTS

| WO | 2011032025 A2 | 3/2011 |
| WO | 2012027266 A2 | 3/2012 |

(Continued)

OTHER PUBLICATIONS

Kowada et al. BODIPY-based probed for the fluorescence imaging of biomolecules in living cells. Chem. Soc. Rev. 2015, vol. 44., pp. 4953-4972. (Year: 2015).*

(Continued)

*Primary Examiner* — Shafiqul Haq
(74) *Attorney, Agent, or Firm* — Shackelford, Bowen, McKinley & Norton, LLP

(57) ABSTRACT

The present invention provides fluorescent compounds of formula (I) as disclosed herein or pharmaceutically acceptable salts thereof. Further provided are uses of said fluorescent compounds in methods of determining, in a sample, the presence and/or amount of pluripotent stem cells or cells undergoing reprogramming to become induced pluripotent stem cells.

(Continued)

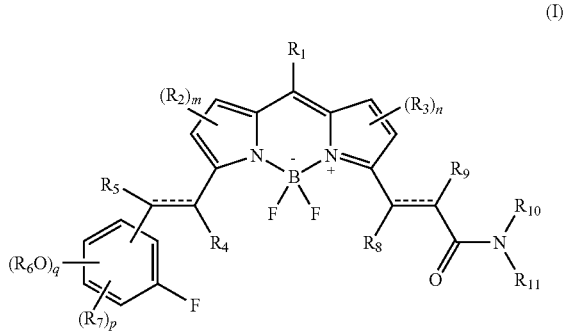

2 Claims, 15 Drawing Sheets

Specification includes a Sequence Listing.

(51) Int. Cl.
C07F 5/02 (2006.01)
C12N 5/074 (2010.01)

(56) References Cited

FOREIGN PATENT DOCUMENTS

| WO | 2012071012 A2 | 5/2012 |
| WO | 2012173575 A1 | 12/2012 |
| WO | 2014109713 A1 | 7/2014 |
| WO | 2016073385 A1 | 5/2016 |

OTHER PUBLICATIONS

Technical Bulletin. Identification of viable stem and progenitor cells with aldeflour. www.stemcell.com; StemCell Technologies Inc.; 2009, North America, Version 1.0.1, pp. 1-4 (Year: 2009).*
International Search Report for International Application No. PCT/SG2018/050329 dated Sep. 26, 2018, pp. 1-4.
Written Opinion of the International Searching Authority for International Application No. PCT/SG2018/050329 dated Sep. 26, 2018, pp. 1-4.
Jeong et al., "CDy6, a Photostable Probe for Long-Term Real-Time Visualization of Mitosis and Proliferating Cells," Chemistry & Biology, vol. 22, No. 2, Feb. 19, 2015, pp. 299-307.
Ong et al., "Identification of Specific Cell-Surface Markers of Adipose-Derived Stem Cells from Subcutaneous and Visceral Fat Depots," Stem Cell Reports, vol. 2, No. 2, Feb. 11, 2014, pp. 171-179.
Takeda et al., "Retinoic Acid Mediates Visceral-Specific Adipogenic Defects of Human Adipose-Derived Stem Cells," Diabetes, vol. 65, No. 5, May 2016, pp. 1164-1178.
Sugii et al., "Feeder-Independent iPS Cell Derivation from Human and Mouse Adipose Stem Cells," Nature Protocols, vol. 6, No. 3, Mar. 2011, pp. 346-358.
Im et al., "A Fluorescent Rosamine Compound Selectively Stains Pluripotent Stem Cells," Angewandte Chem., vol. 49, No. 41, 2010, pp. 7497-7500.
Kang et al., "Embryonic and Induced Pluripotent Stem Cell Staining and Sorting with the Live-Cell Fluorescence Imaging Probe CDy1," Nature Protocols, vol. 6, No. 7, 2011, pp. 1044-1052.
Kim et al., "TopHat2: Accurate Alignment of Transcriptomes in the Presence of Insertions, Deletions and Gene Fusions," Genome Biology, vol. 14, No. 4, 2013, p. 1-13.
Trapnell et al., "Transcript Assembly and Abundance Estimation from RNA-Seq Reveals Thousands of New Transcripts and Switching Among Isoforms," Nat Biotechnol., vol. 28, No. 5, May 2010, pp. 511-515.
Ghosh et al., "The Development of a Nucleus Staining Fluorescent Probe for Dynamic Mitosis Imaging in Live Cells," Chem. Commun., vol. 51, No. 45, 2015, pp. 9336-9338.
Atari et al., "Dental Pulp of the Third Molar: A New Source of Pluripotent-Like Stem Cells," Journal of Cell Science, vol. 125, Feb. 13, 2012, pp. 3343-3356.
Chan et al., "Live Cell Imaging Distinguishes Bona Fide Human iPS Cells from Partially Reprogrammed Cells," Nature Biotechnology, vol. 27, No. 11, Nov. 2009, pp. 1033-1037.
Fritz et al., "cAMP and EPAC Signaling Functionally Replace OCT4 During Induced Pluripotent Stem Cell Reprogramming," Molecular Therapy, vol. 23, No. 5, May 2015, pp. 952-963.
Hirata et al., "A Chemical Probe that Labels Human Pluripotent Stem Cells," Cell Reports, vol. 6, Mar. 27, 2014, pp. 1165-1174.
Hotta et al., "Isolation of Human iPS Cells Using EOS Lentiviral Vectors to Select for Pluripotency," Nature Methods, vol. 6, No. 5, May 2009, pp. 370-376.
Hou et al., "Pluripotent Stem Cells Induced from Mouse Somatic Cells by Small-Molecule Compounds," Sciencexpress, vol. 341, Jul. 18, 2013, pp. 651-654.
Li et al., Looking to the Future Following 10 Years of Induced Pluripotent Stem Cell Technologies, Nature Protocols, vol. 11, No. 9, 2016, pp. 1579-1585.
Li et al., "A Mesenchymal-to-Epithelial Transition Initiates and is Required for the Nuclear Reprogramming of Mouse Fibroblasts," Cell Stem Cell, vol. 7, Jul. 2, 2010, pp. 51-63.
Luo et al., "Generation of GFP Reporter Human Induced Pluripotent Stem Cells Using AAVS1 Safe Harbor Transcription Activator-Like Effector Nuclease," Curr Protoc Stem Cell Biol., vol. 29, May 16, 2015, pp. 1-18.
Okita et al., A More Efficient Method to Generate Integration-Free Human iPS Cells, Nature Methods, vol. 8, 2011, pp. 409-412.
Ovchinnikov et al., "Transgenic Human ES and iPS Reporter Cell Lines for Identification and Selection of Pluripotent Stem Cells in Vitro," Stem Cell Research, vol. 13, 2014, pp. 251-261.
Pistollato et al., "Development of a Pluripotent Stem Cell Derived Neuronal Model to Identify Chemically Induced Pathway Perturbations in Relation to Neurotoxicity: Effects of CREB Pathway Inhibition," Toxicology and Applied Pharmacology, vol. 280, 2014, pp. 378-388.
Quintanilla, Jr., et al., "Kinetic Measurement and Real Time Visualization of Somatic Reprogramming," Journal of Visualized Experiments, vol. 113, Jul. 2016, pp. 1-11.
Riekstina et al., "Embryonic Stem Cell Marker Expression Pattern in Human Mesenchymal Stem Cells Derived from Bone Marrow, Adipose Tissue, Heart and Dermis," Stem Cell Rev and Rep, vol. 5, 2009, pp. 378-386.
Samavarchi-Tehrani et al., "Functional Genomics Reveals a BMP-Driven Mesenchymal-to-Epithelial Transition in the Initiation of Somatic Cell Reprogramming," Cell Stem Cell, vol. 7, Jul. 2, 2010, pp. 64-77.
Sugii et al., "Human and Mouse Adipose-Derived Cells Support Feeder-Independent Induction of Pluripotent Stem Cells," PNAS, vol. 107, No. 8, Feb. 23, 2010, pp. 3558-3563.
Takahashi et al., "Induction of Pluripotent Stem Cells from Adult Human Fibroblasts by Defined Factors," Cell, vol. 131, Nov. 30, 2007, pp. 861-872.
Takahashi et al., "A Decade of Transcription Factor-Mediated Reprogramming to Pluripotency," Nature Reviews Molecular Cell Biology, vol. 17, Mar. 2016, pp. 183-193.
Kurosawa, Hiroshi, "Methods for Inducing Embryoid Body Formation: In Vitro Differentiation System of Embryonic Stem Cells," Journal of Bioscience and Bioengineering, vol. 103, No. 5, 2007, pp. 389-398.
Toh et al., "RNAi Reveals Phase-Specific Global Regulators of Human Somatic Cell Reprogramming," Cell Reports, vol. 15, No. 12, Jun. 21, 2016, pp. 2597-2607.
Lahm et al., "Live Fluorescent RNA-Based Detection of Pluripotency Gene Expression in Embryonic and Induced Pluripotent Stem Cells of Different Species," Stem Cells, vol. 33, No. 2, Feb. 2015, pp. 392-402.

(56) References Cited

OTHER PUBLICATIONS

Zhai et al., "Synthesis of a Novel BODIPY Library and Its Application in the Discovery of a Fructose Sensor," ACS Combinatorial Science, vol. 14, No. 2, Jan. 20, 2012, pp. 81-84.
Zhang, et al., "Discovery of a Structural-Element Specific G-Quadruplex "Light-Up" Probe," Scientific Reports, vol. 4, No. 3776, Jan. 20, 2014, pp. 1-6.
Yun et al., "Neural Stem Cell Specific Fluorescent Chemical Probe Binding to FABP7," PNAS, vol. 109, No. 26, Jun. 26, 2012, pp. 10214-10217.
Kowada, et al., "BODIPY-Based Probes for the Fluorescence Imaging of Biomolecules in Living Cells," Chem. Soc. Rev., vol. 44, No. 14, Mar. 24, 2015, pp. 4953-4972.

* cited by examiner

Figure 1
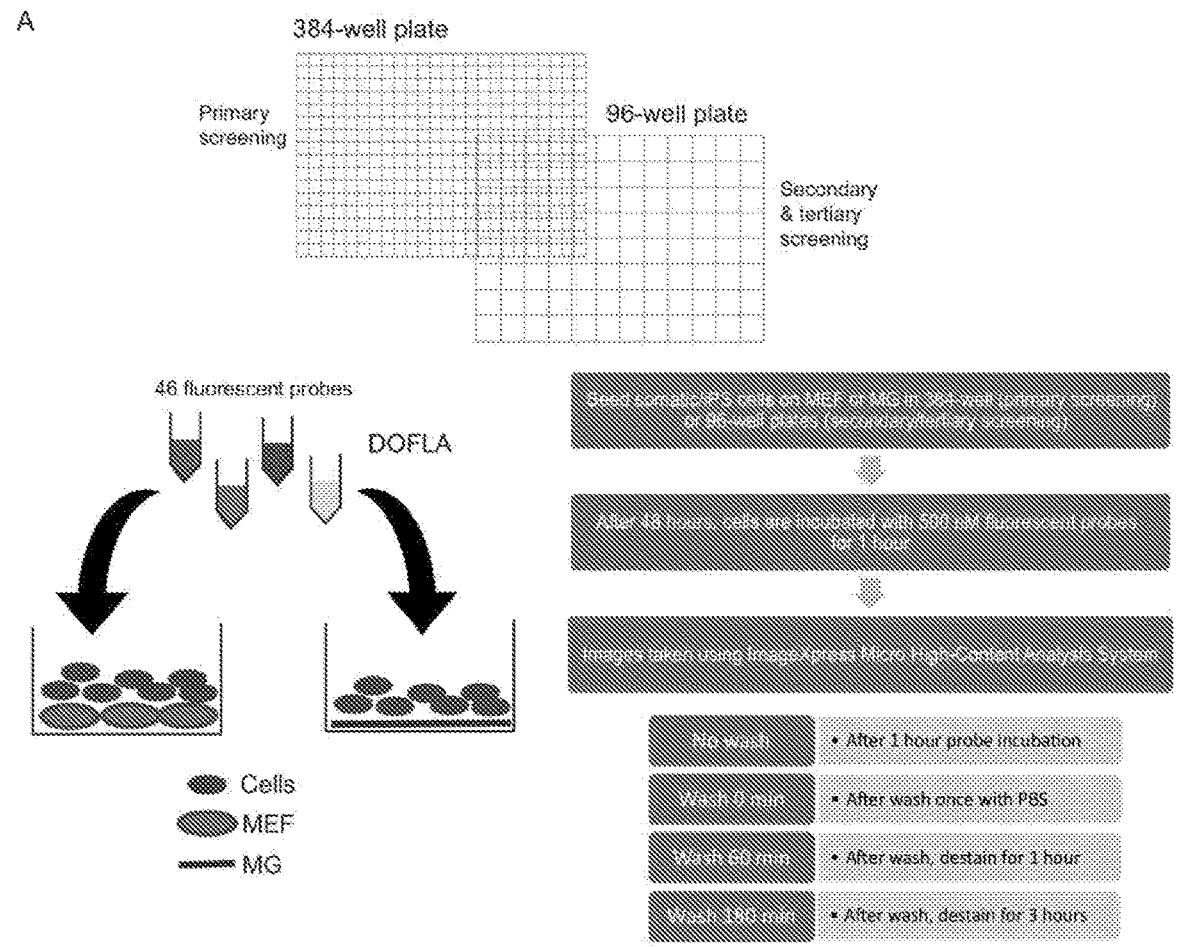
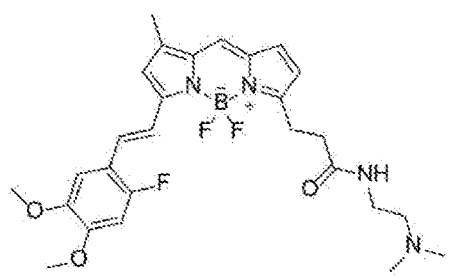
Chemical Formula: $C_{27}H_{32}BF_3N_4O_3$
Molecular Weight: 528.38
BDL305
BDL-E5

Figure 10
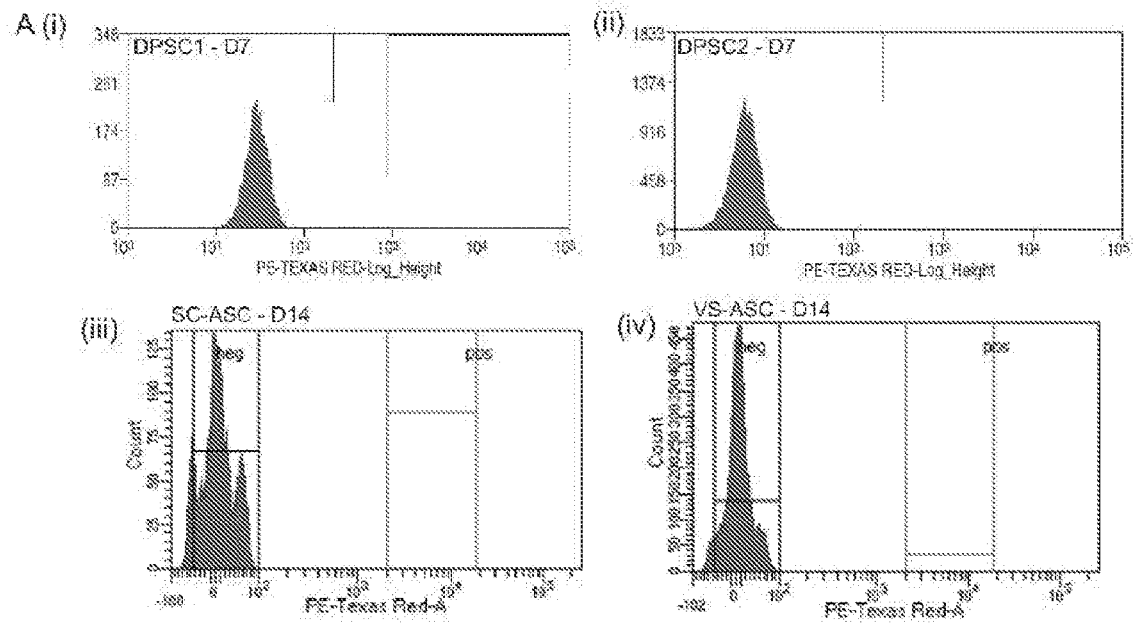
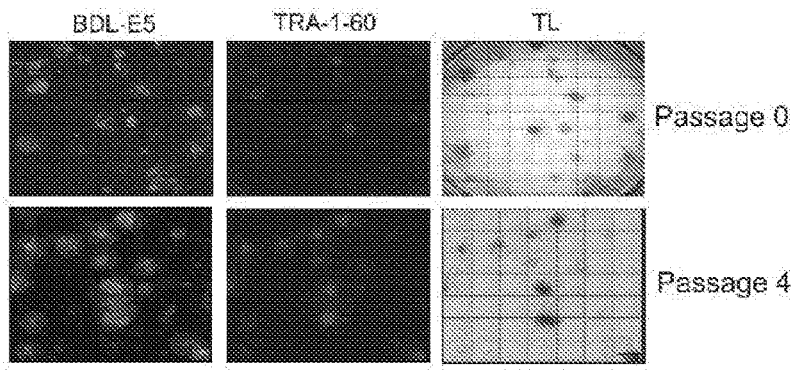
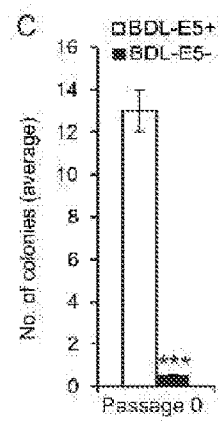
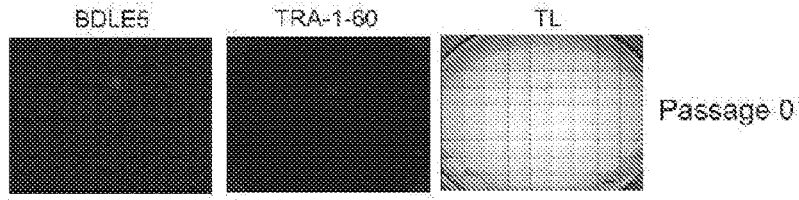

Figure 12
A
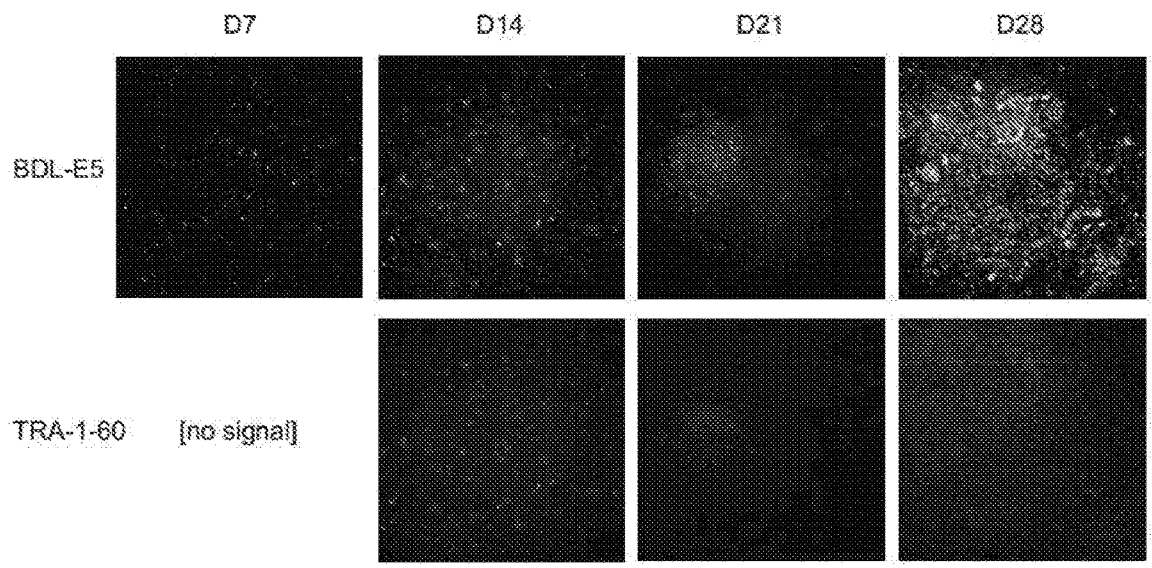
B
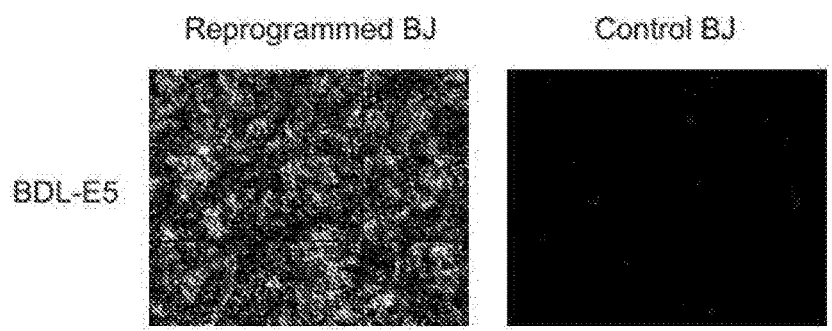
C

Figure 13

A   BDL-E5+ vs. BDL-E5- cells

| ID | Associated Network Functions | Score |
|---|---|---|
| 1 | Embryonic Development, Organismal Development, Tissue Development | 38 |
| 2 | Cell Death and Survival, Cell Signaling, Nucleic Acid Metabolism | 20 |
| 3 | Cancer, Cardiovascular Disease, Developmental Disorder | 20 |
| 4 | Cell Morphology, Cellular Development, Cellular Growth and Proliferation | 17 |
| 5 | Cell Morphology, Organ Morphology, Reproductive System Development and Function | 15 |

Top Canonical Pathways

| Name | p-value |
|---|---|
| BMP signaling pathway | 2.01E-04 |
| FGF Signaling | 2.65E-03 |
| Agrin Interactions at Neuromuscular Junction | 4.70E-03 |
| Cdc42 Signaling | 5.24E-03 |
| Paxillin Signaling | 5.35E-03 |

| Molecular and Cellular Functions | p-value |
|---|---|
| Cell-To-Cell Signaling and Interaction | 4.81E-02 - 7.85E-04 |
| Cellular Assembly and Organization | 4.81E-02 - 7.85E-04 |
| Cellular Growth and Proliferation | 4.93E-02 - 7.85E-04 |
| Gene Expression | 4.63E-02 - 1.36E-03 |
| Cell Death and Survival | 4.81E-02 - 2.56E-03 |

B   Enriched Clusters - BDL-E5+ vs. BDL-E5- cells

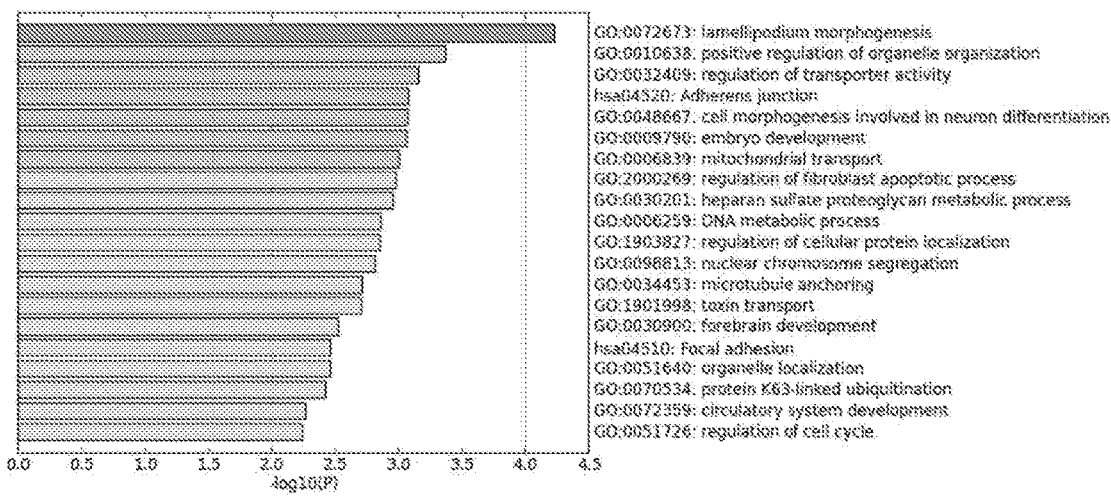

SEQUENCE LISTING

```
<160> NUMBER OF SEQ ID NOS: 42

<210> SEQ ID NO 1
<211> LENGTH: 23
<212> TYPE: DNA
<213> ORGANISM: Artificial Sequence
<220> FEATURE:
<223> OTHER INFORMATION: primer

<400> SEQUENCE: 1
caaggtcatc catgacaact ttg                                           23

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ggccatccac agtcttctgg                                               20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
ctcggagatc atcacgtttg                                               20

<210> SEQ ID NO 4
<211> LENGTH: 20
```

```
<212> TYPE: DNA
<213> ORGANISM: Artificial Sequence
<220> FEATURE:
<223> OTHER INFORMATION: primer

<400> SEQUENCE: 4
ccttggaaat ctcgaagtgc                                              20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gaagcgcaga tcaaaaggag                                              20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gctgatgctc tggcagaagt                                              20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ccaacatcct gaacctcagc                                              20

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
gctattcttc ggccagttg                                               19

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
tggtgtcaac aactcggttt g                                            21

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
```

```
ctcgaacatc gctgtaatct gg                                              22

<210> SEQ ID NO 11
<211> LENGTH: 18
<212> TYPE: DNA
<213> ORGANISM: Artificial Sequence
<220> FEATURE:
<223> OTHER INFORMATION: primer

<400> SEQUENCE: 11
gcagcacgtg gagctgta                                                   18

<210> SEQ ID NO 12
<211> LENGTH: 18
<212> TYPE: DNA
<213> ORGANISM: Artificial Sequence
<220> FEATURE:
<223> OTHER INFORMATION: primer

<400> SEQUENCE: 12
cagccggttg ctgaggta                                                   18

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
ctggccgaaa atacattgta aa                                              22

<210> SEQ ID NO 14
<211> LENGTH: 18
<212> TYPE: DNA
<213> ORGANISM: Artificial Sequence
<220> FEATURE:
<223> OTHER INFORMATION: primer

<400> SEQUENCE: 14
ccacagtcgg gtcaggag                                                   18

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
tacacagacg tgtccaacat gggc                                            24

<210> SEQ ID NO 16
<211> LENGTH: 24
<212> TYPE: DNA
<213> ORGANISM: Artificial Sequence
<220> FEATURE:
<223> OTHER INFORMATION: primer

<400> SEQUENCE: 16
ggatgccttc aggaatcaca cctc                                            24

<210> SEQ ID NO 17
<211> LENGTH: 20
<212> TYPE: DNA
<213> ORGANISM: Artificial Sequence
```

```
<220> FEATURE:
<223> OTHER INFORMATION: primer

<400> SEQUENCE: 17
aaatgtttgt gttgcggtca                                              20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
tctggcacag gtgtcttcag                                              20

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
gaaggtgaca gagcctctgg at                                           22

<210> SEQ ID NO 20
<211> LENGTH: 23
<212> TYPE: DNA
<213> ORGANISM: Artificial Sequence
<220> FEATURE:
<223> OTHER INFORMATION: primer

<400> SEQUENCE: 20
gatcggttac cgtgatcaaa atc                                          23

<210> SEQ ID NO 21
<211> LENGTH: 13
<212> TYPE: DNA
<213> ORGANISM: Artificial Sequence
<220> FEATURE:
<223> OTHER INFORMATION: primer

<400> SEQUENCE: 21
tgtgtgcgtg gga                                                     13

<210> SEQ ID NO 22
<211> LENGTH: 21
<212> TYPE: DNA
<213> ORGANISM: Artificial Sequence
<220> FEATURE:
<223> OTHER INFORMATION: primer

<400> SEQUENCE: 22
ttcaagattg gtaaagccag t                                            21

<210> SEQ ID NO 23
<211> LENGTH: 23
<212> TYPE: DNA
<213> ORGANISM: Artificial Sequence
<220> FEATURE:
<223> OTHER INFORMATION: primer

<400> SEQUENCE: 23
agcagtgaaa gagaagggaa tgc                                          23
```

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
ggtcctcttc aggtgcctca g                                     21

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
cgcagcacat gaatcacagg                                       20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
cgtatcgttt cgggatccgt                                       20

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
tctgaggcca aggatctcca                                       20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
cattcgggag aaggtccgag                                       20

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
tcatctttgg ggcgagtgag                                       20

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
tccttgaagc aaccagggtc                                                     20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
attggaagga aaggggaggg                                                     20

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
ggcttgaaca catcttggca                                                     20

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
cagtagagtg gggcaggaaa                                                     20

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
tcccatttca catctgggct                                                     20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
aaggctcgtt cctgttcaga                                                     20

<210> SEQ ID NO 36
<211> LENGTH: 19
<212> TYPE: DNA
<213> ORGANISM: Artificial Sequence
<220> FEATURE:
<223> OTHER INFORMATION: primer

<400> SEQUENCE: 36
ggcattgcac aggtagtgg                                                      19

<210> SEQ ID NO 37

```
<211> LENGTH: 20
<212> TYPE: DNA
<213> ORGANISM: Artificial Sequence
<220> FEATURE:
<223> OTHER INFORMATION: primer

<400> SEQUENCE: 37
gagcagtgtg gacacgtacc                                                    20

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
gtccagggga gacatttcag                                                    20

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
ctgttccagc catccttcat                                                    20

<210> SEQ ID NO 40
<211> LENGTH: 22
<212> TYPE: DNA
<213> ORGANISM: Artificial Sequence
<220> FEATURE:
<223> OTHER INFORMATION: primer

<400> SEQUENCE: 40
tcatgatgct gttgtaggtg gt                                                 22

<210> SEQ ID NO 41
<211> LENGTH: 23
<212> TYPE: DNA
<213> ORGANISM: Artificial Sequence
<220> FEATURE:
<223> OTHER INFORMATION: primer

<400> SEQUENCE: 41
aagaatttca gcatgatttt cca                                                23

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
cacccacttc atggttgcta                                                    20
```

FLUORESCENT COMPOUNDS SPECIFIC FOR PLURIPOTENT STEM CELLS AND REPROGRAMMING-READY CELLS AND METHODS OF USING THE SAME

CROSS-REFERENCE TO RELATED APPLICATION

This application refers to and claims the benefit of priority of the Singapore Patent Application No. 10201705493P filed on 4 Jul. 2017, the content of which is incorporated herein by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention relates generally to compounds specific for pluripotent stem cells and reprogramming cells and the methods of using the same.

BACKGROUND OF THE INVENTION

The discovery of human induced pluripotent stem (iPS) cells has revolutionized and accelerated the new development of personalized drug screening, human disease modeling, and regenerative therapeutics. Despite rapid development of methods to derive human iPS cells, there have been several problems and challenges with the reprogramming protocols. These include relatively low efficiency of obtaining high quality cells, long duration of complete reprogramming processes (typically 3-4 weeks before colony formation), and difficulty in prompt analysis and identification of high quality iPS cells. The low efficiency and long time-course worsen when clinically applicable protocols are attempted by adapting non-viral transduction and feeder-free reprogramming methods. Efficiency and time can be improved using selective cell types. For example, the inventors of the present application previously found that adipose-derived stem cells (ASCs) and dental pulp-derived stem cells (DPSCs) allow feeder-free reprogramming with relatively high efficiencies and shorter time frames.

However, the technology to promptly distinguish bona fide pluripotent stem cells from other somatic cell populations is still underdeveloped. Traditionally, gene reporters such as fluorescent proteins driven under OCT4, NANOG, or artificial reporters have been used. However, these constructs need to be inserted into cells by viral, gene editing or other genetic engineering methods and successful expression verified, which are cumbersome and potentially disruptive to endogenous genome function and are not widely applicable for diverse ranges of cell types.

Using fluorescent dye conjugated antibodies for pluripotent cell surface markers such as TRA-1-60/81 and SSEA3/4, or fluorescent substrates for alkaline phosphatase is the most common method to detect iPS cells (Quintanilla, et al., (2016). J Vis Exp.). However, alkaline phosphatase and SSEA3/4 are not very specific to bona fide pluripotent stem cells, and are detectable in adult stem cells including adipose-derived stromal cells (ASCs) and dental pulp stem cells (DPSCs). All these markers typically stain well-developed colonies of iPS cells only, which can be visible and recognized by experienced observers even under phase contrast microscopy. In addition, it is relatively expensive to manufacture these fluorescent probes, which may hinder the clinical and commercial development of iPS technology.

KP-1 is a fluorescent probe that is reportedly specific for human iPS cells. However, it fails to enable the sorting of early reprogramming cells to enrich colony-forming iPS cells (Hirata et al., 2014). The inventors previously identified CDy1, a small-molecule fluorescent probe, by screening against mouse ES and iPS cells (Im, et al. (2010). Angew Chem Int Ed Engl 49, 7497-7500; Kang, et al. (2011). Nat Protoc 6, 1044-1052). CDy1 allowed early stage live cell staining and sorting of reprogramming cells.

However, there remains a considerable need for new fluorescent probes that specifically detect iPS cells at an early reprogramming stage.

SUMMARY OF THE INVENTION

The inventors of the present invention have found that said need can be met by the provision of the fluorescent compounds disclosed herein.

In a first aspect, the present invention relates to a fluorescent compound of formula (I) or a pharmaceutically acceptable salt thereof

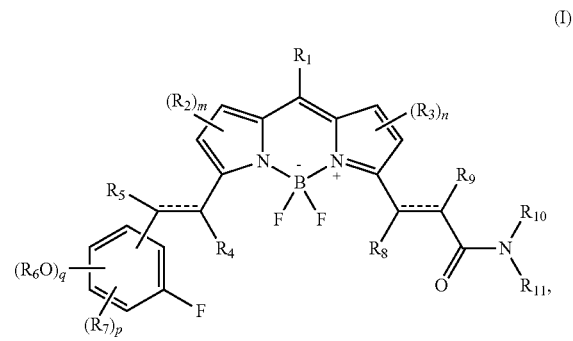

(I)

wherein:

$R_1$, $R_4$, $R_5$, $R_8$, $R_9$ and $R_{10}$ are each independently selected from the group consisting of H and $C_{1-6}$ alkyl;

$R_2$, $R_3$, $R_6$ and $R_7$ are each independently selected from $C_{1-6}$ alkyl;

$R_{11}$ is selected from the group consisting of H, $(CR_{12}R_{13})_o$—$N(R_{14}R_{15})$ and $C_{1-6}$ alkyl, wherein o is independently 0, 1, 2, 3, 4, or 5, and $R_{12}$-$R_{15}$ are each independently selected from the group consisting of H and $C_{1-6}$ alkyl;

m and n are each independently 0, 1, or 2;

p is 0, 1, 2, or 3, q is 1, 2, 3, or 4, with the proviso that p+q≤4; and

--- means that the respective bond can be a single or double bond and, if it is a single bond, the additional valencies are hydrogen.

In various embodiments, $R_1$, $R_4$, $R_5$, $R_8$, $R_9$ and $R_{10}$ are each independently selected from the group consisting of hydrogen and methyl and/or $R_2$, $R_3$, $R_6$ and $R_7$ are each methyl and/or $R_{11}$ is $(CH_2)_2$—$N(CH_3)_2$.

In preferred embodiments, the fluorescent compound is a compound of formula (II)

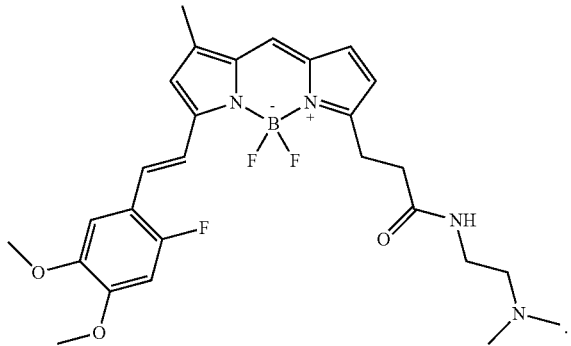

(II)

In a second aspect, the invention relates to a method of determining, in a sample, the presence and/or amount of pluripotent stem cells, said method comprising the steps of:
(i) providing a sample suspected of containing one or more pluripotent stem cells;
(ii) contacting the sample with a fluorescent compound disclosed herein under conditions that allow binding of said fluorescent compound to the pluripotent stem cells; and
(iii) determining the presence and/or amount of the pluripotent stem cells by measuring the fluorescence of the cells following said contacting.

In various embodiments, the pluripotent stem cells are embryonic stem cells or induced pluripotent stem cells.

In various embodiments, the pluripotent stem cells are mammalian cells, preferably human, mouse, or rat cells, more preferably human cells.

In various embodiments, step (ii) does not comprise a washing step following said contacting.

In various embodiments, the method further comprises a step of:
(iv) isolating the pluripotent stem cells labelled by the fluorescent compound from the sample.

In various embodiments, the labelled cells are isolated by fluorescence-activated cell sorting (FACS).

In a third aspect, the invention relates to a method of determining, in a sample, the presence and/or amount of cells undergoing reprogramming to become induced pluripotent stem cells, said method comprising the steps of:
(i) providing a sample suspected of containing one or more cells undergoing reprogramming to become induced pluripotent stem cells;
(ii) contacting the sample with a fluorescent compound disclosed herein under conditions that allow binding of said fluorescent compound to the cells undergoing reprogramming to become induced pluripotent stem cells; and
(iii) determining the presence and/or amount of the cells undergoing reprogramming to become induced pluripotent stem cells by measuring the fluorescence of the cells following said contacting.

In various embodiments, the cells undergoing reprogramming to become induced pluripotent stem cells are mammalian cells, preferably human, mouse, or rat cells, more preferably human cells.

In various embodiments, step (ii) does not comprise a washing step following said contacting.

In various embodiments, the method further comprises a step of:
(iv) isolating the cells undergoing reprogramming to become induced pluripotent stem cells labelled by the fluorescent compound from the sample.

In various embodiments, the labelled cells are isolated by fluorescence-activated cell sorting (FACS).

In a fourth aspect, the invention relates to the use of the fluorescent compound disclosed herein in the detection and/or isolation of pluripotent stem cells.

In another aspect, the invention relates to the use of the fluorescent compound disclosed herein in the detection and/or isolation of cells undergoing reprogramming to become induced pluripotent stem cells.

BRIEF DESCRIPTION OF THE DRAWINGS

The invention will be better understood with reference to the detailed description when considered in conjunction with the non-limiting examples and the accompanying drawings.

FIG. 1: (A) Schematic diagram showing the screening process of fluorescent probes for somatic and iPS cells using DOFLA. Cells were seeded on either MEFs or MG in 384-well plates for primary screening and 96-well plates for secondary and tertiary screening. After 48 h, cells were stained with probes for 1 h and images were taken in the ImageXpress under various conditions as indicated. (B) The chemical structure of BDL-E5.

FIG. 10: (A) (i)-(iv) Histogram (FACS) showing unstained populations of cells used as the control for FACS performed in FIG. 4. (B) Fluorescence images of BDL-E5, TRA-1-60 and transmitted light (TL) images showing iPS colonies derived from ASC4 14 dpn BDL-E5$^+$ (i) and BDL-E5$^-$ (ii) cells at passage 0 (4×) and passage 4 (10×)

(n=3). Scale bar represents 100 µm. (C) Graph showing average number of iPS colonies from BDL-E5$^+$ and BDL-E5$^-$ cell populations at 14 dpn in ASC4 at passage 0 (n=3). ***p<0.001 denotes statistical significance.

Figure 11:
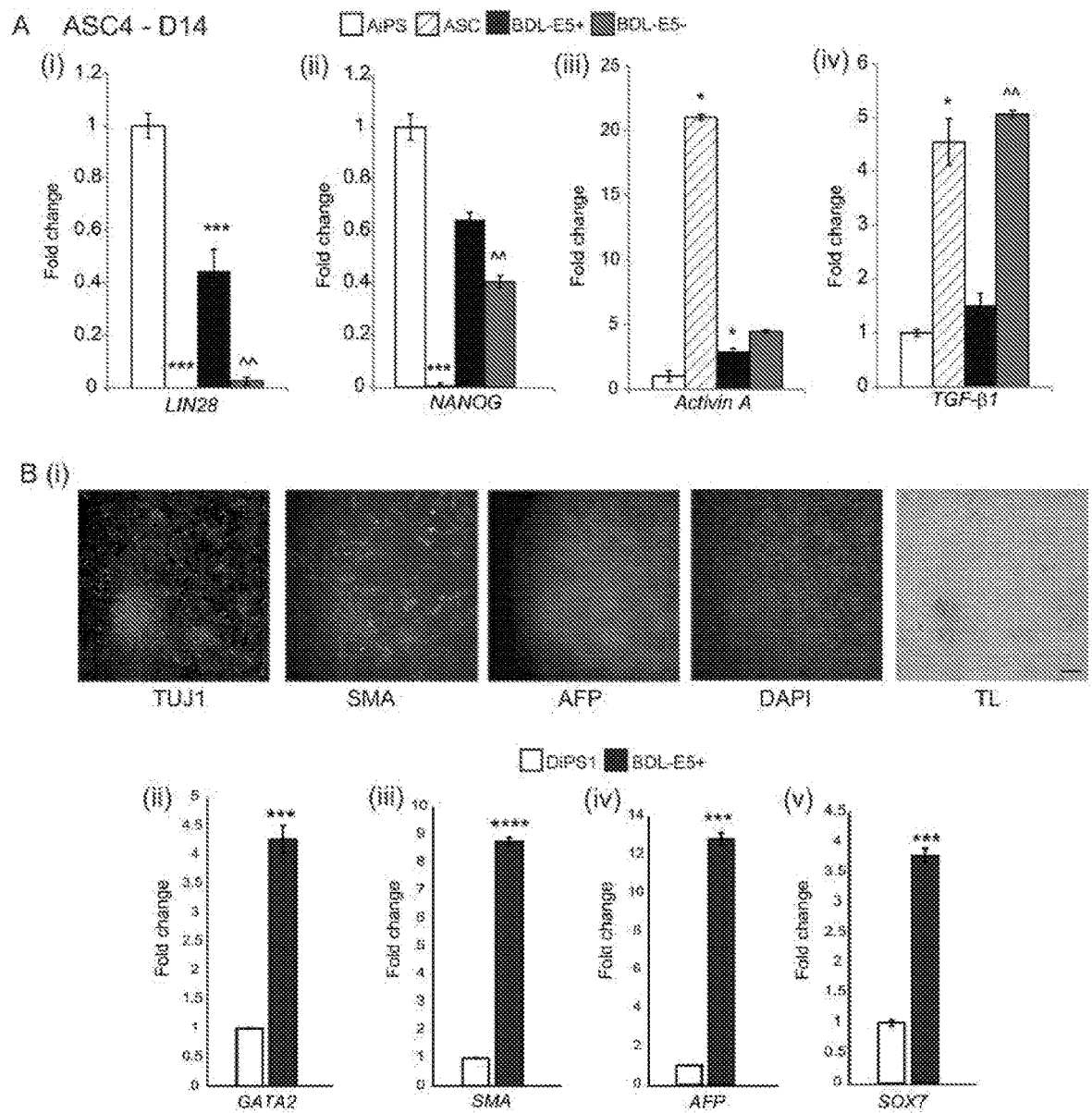
Figure 11:
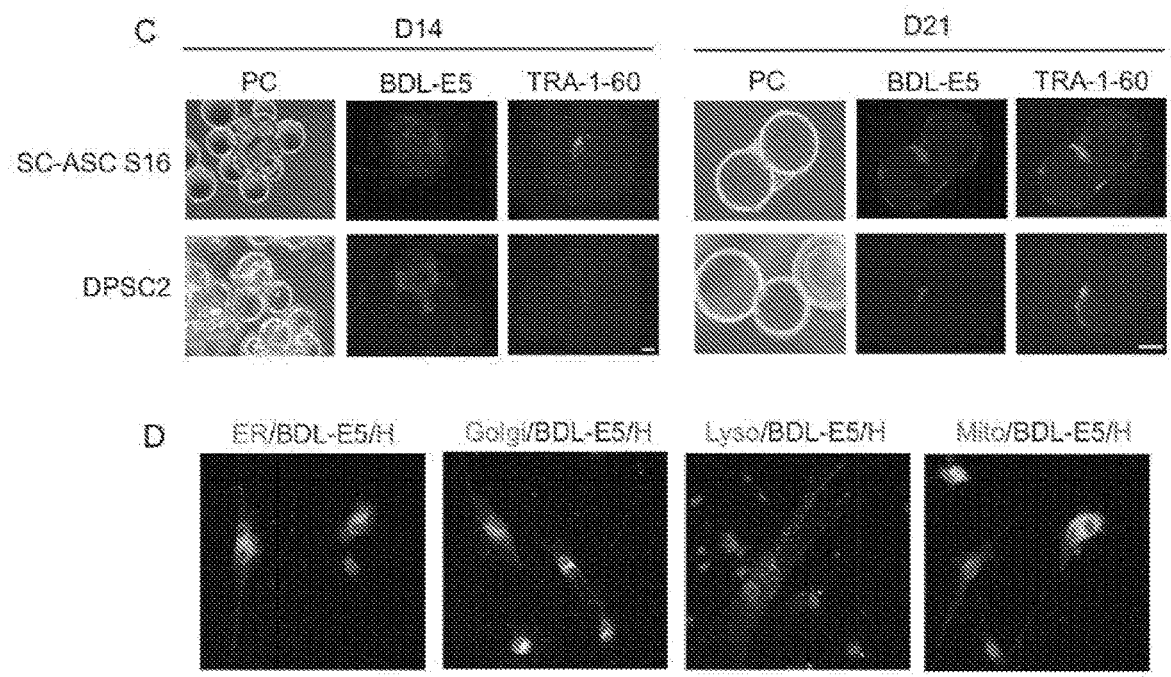

FIG. 11: (A) Representative graphs showing gene expression of LIN28 (i), NANOG (ii), Activin A (iii) and TGF-β1 (iv) in RNA isolated from AiPS4, ASC4, BDL-E5$^+$ and BDL-E5$^-$ cells of ASC4 at 14 dpn. *p<0.05 and *p<0.001 denote significance compared with AiPS4; ^^p<0.01 denotes significance compared with BDL-E5$^+$ (n=3). (B) (i) Fluorescence images (10×) of TUJ1, SMA, AFP, DAPI and TL of cells following spontaneous differentiation of EBs generated from BDL-E5$^+$ DPSC1. (ii)-(v) Representative graphs showing gene expression of GATA2, SMA, AFP and SOX7 in RNA isolated from DiPS1 and spontaneously differentiated cells from EBs formed from BDL-E5$^+$ iPS cells. *p<0.001 and ****p<0.0001 denote significance compared with DiPS1 (n=3). (C) Phase contrast (PC) and fluorescent images of BDL-E5 and TRA-1-60 of reprogramming SC-ASC S16 and DPSC2 on Geltrex™-coated Cytodex 3 microcarriers at 14 dpn (10×) and 21 dpn (20×). Scale bar represents 100 µm. (D) Fluorescent images of reprogramming DPSC2 on MG coated chamber slides at 7 dpn (n=3). These images are zoomed in and cropped from 20× images to clearly show the stains and their overlap; green—markers for Endoplasmic Reticulum (ER), Golgi, Lysosome, or Mitochondria; red—BDL-E5; blue—Hoechst 33342.

FIG. 12: (A) DPSC1 was reprogrammed with the traditional method involving retroviral OCT4, SOX2, KLF4 and C-MYC, and plated onto the MEF feeder layer. Cells were co-stained with BDL-E5 and TRA-1-60 in the indicated day post-infection (dpi). (B) BJ fibroblasts were transduced with lentiviral OCT4, SOX2, KLF4 and C-MYC in the presence or absence of A83-01 (0.3 µM) and stained at 8 dpi. The image is merged from 9 independent fields. (C) BJ fibroblasts transduced above were stained with BDL-E5 followed by cell fixation and immunostaining with TRA-1-60 at 21 dpi.

FIG. 13: (A) Pathway analysis using Ingenuity Systems (Qiagen) shows representation of the top networks and canonical pathways between BDL-E5$^+$ and BDL-E5$^-$ cells. The molecular and cellular functions that were differentially expressed in BDL-E5$^+$ and BDL-E5$^-$ cells are also represented, along with the p values. (B) Metascape gene analysis was performed on http://metascape.org and the enriched clusters between BDL-E5$^+$ vs. BDL-E5$^-$ cells are represented here.

Figure 14:
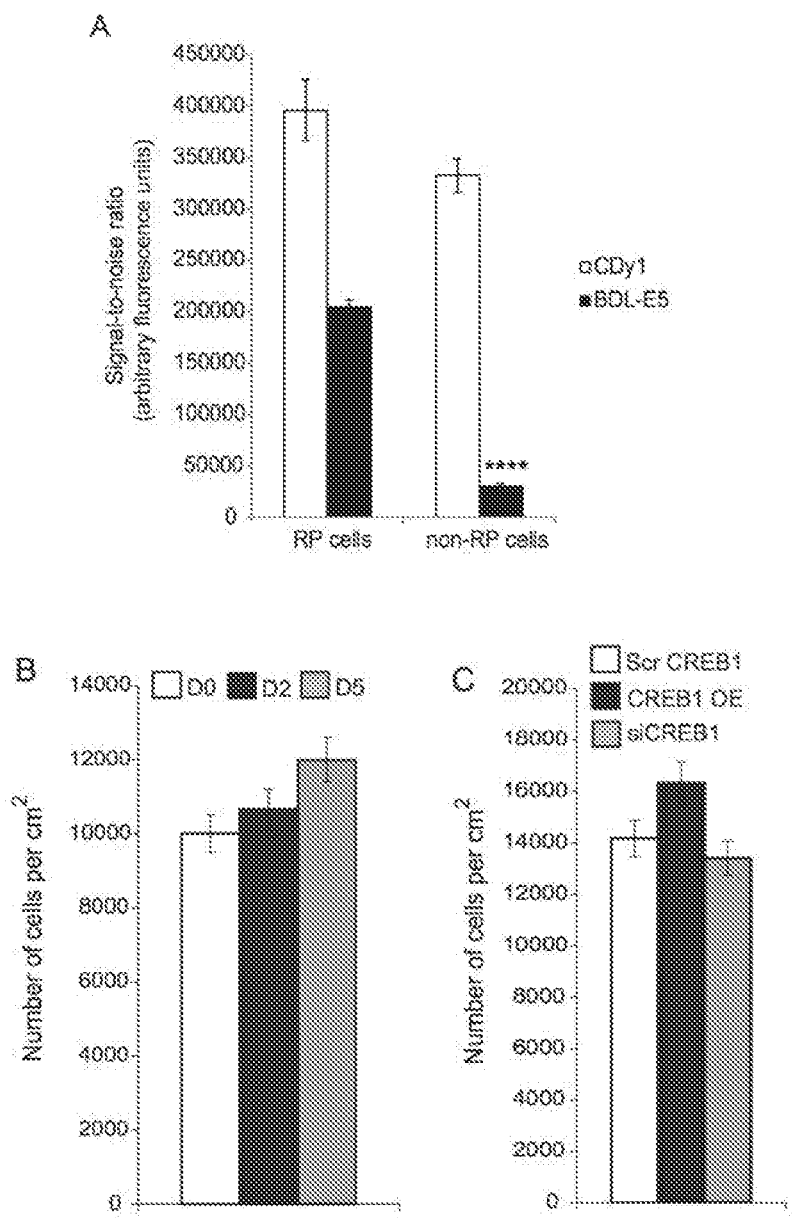

FIG. 14: (A) Graph representing signal-to-noise ratios (arbitrary fluorescence units) on comparing reprogramming (RP) versus non-reprogramming (non-RP) DPSCs (DPSC1) stained with either CDy1 or BDL-E5. The fluorescence intensity was measured using ImageJ software. 100 cells per field (10×), 10 fields per well, 3 wells per probe were measured. ****p<0001 denotes significance between RP and non-RP cells. (B) Proliferation assay of DPSC1 incubated with BDL-E5 (500 nM) for 2 to 5 days; represented as number of viable cells per cm$^2$ (n=3). (C) Proliferation assay of reprogramming DPSC1, 48 h after transfection with Scr CREB1, CREB1 OE or siCREB1; represented as number of viable cells per cm$^2$ (n=3).

DETAILED DESCRIPTION OF THE INVENTION

The following detailed description refers to, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Unless otherwise defined, all technical and scientific terms used herein have the same meaning as commonly understood by one of ordinary skill in the art. The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

In a first aspect, the present invention relates to a fluorescent compound of formula (I) or a pharmaceutically acceptable salt thereof

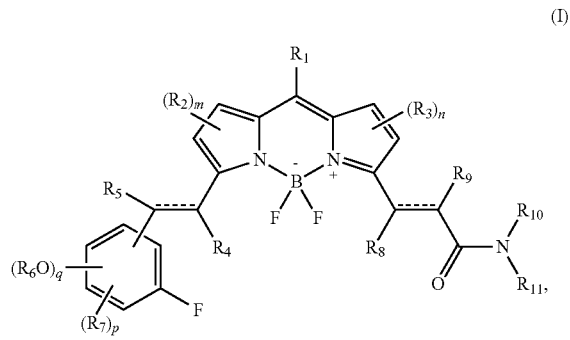

(I)

wherein:
$R_1$, $R_4$, $R_5$, $R_8$, $R_9$ and $R_{10}$ are each independently selected from the group consisting of H and $C_{1-6}$ alkyl;
$R_2$, $R_3$, $R_6$ and $R_7$ are each independently selected from $C_{1-6}$ alkyl;
$R_{11}$ is selected from the group consisting of H, $(CR_{12}R_{13})_o$—$N(R_{14}R_{15})$ and $C_{1-6}$ alkyl, wherein o is independently 0, 1, 2, 3, 4, or 5, and $R_{12}$-$R_{15}$ are each independently selected from the group consisting of H and $C_{1-6}$ alkyl;
m and n are each independently 0, 1, or 2;
p is 0, 1, 2, or 3,
q is 1, 2, 3, or 4, with the proviso that p+q≤4; and
═══ means that the respective bond can be a single or double bond and, if it is a single bond, the additional valencies are hydrogen.

The term "fluorescent compound" as used herein refers to a compound having a functional group or moiety which will molecularly absorb photonic energy of a specific UV wavelength and subsequently re-emit of at least a portion of the absorbed energy as photonic energy at a different wavelength within the visible light range, i.e. 380 to 700 nm.

Determining whether a compound falling within formula (I) is a fluorescent compound is within the knowledge of the person of average skill in the art. For example, fluorescence microscopy, fluorescence spectrometry, and flow cytometry can be used to detect a signal emitted by a fluorescent compound of formula (I).

The term "alkyl" as used herein refers to a linear, branched, or cyclic saturated hydrocarbon group. The term "$C_{1-6}$ alkyl" indicates that the group may have from 1 to 6 (inclusive) carbon atoms in it. Representative alkyl groups include methyl, ethyl, n-propyl, i-propyl, n-butyl, t-butyl, n-pentyl, and 3-pentyl and the like.

The term "pharmaceutically acceptable salt" as used herein refers to those salts that are within the scope of proper medicinal assessment, suitable for use in contact with human tissues and organs and those of lower animals, without undue toxicity, irritation, allergic response or similar and are consistent with a reasonable benefit/risk ratio. Pharmaceutically acceptable salts are technically well known.

In various embodiments, $R_1$, $R_4$, $R_5$, $R_8$, $R_9$ and $R_{10}$ are each independently selected from the group consisting of hydrogen and methyl and/or $R_2$, $R_3$, $R_6$ and $R_7$ are each methyl and/or $R_{11}$ is $(CH_2)_2$—$N(CH_3)_2$.

In preferred embodiments, the fluorescent compound is a compound of formula (II)

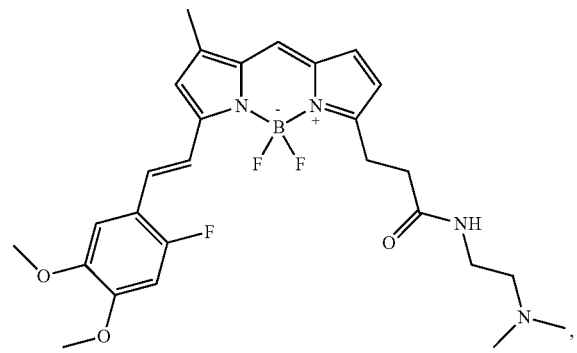

(II)

which is referred to herein as BDL-E5.

Without wishing to be bound to any theory, it is believed that the fluorescent compounds of formulae (I) and (II) are non-toxic and specifically bind to pluripotent stem cells or cells undergoing reprogramming that have been determined to become induced pluripotent stem cells.

As would be readily appreciated by the skilled person, by the term "specific binding" or "specifically bind" is meant that the fluorescent compounds of this disclosure bind to pluripotent stem cells or cells undergoing reprogramming to become induced pluripotent stem cells with a substantially higher selectivity than to non-target cells such as somatic cells, providing for a distinguishing fluorescence signal. Typically, a fluorescence signal indicating the presence and/or amount of said cells is substantially greater than background signal. For example, said fluorescence signal can be at least two-fold greater than the intensity of background fluorescence signal. Preferably, the intensity of the fluorescence signal is at least five-fold, at least ten-fold, and, most preferably, at least fifty-fold greater than the intensity of background fluorescence signal.

The compounds of formula (I) or (II) disclosed herein may be prepared using standard techniques known to those skilled in the art of synthetic organic chemistry, or may be deduced by reference to the pertinent literature, for example, WO2014109713A1, which discloses a synthetic scheme of BODIPY compounds and is hereby incorporated by reference in its entirety.

In a second aspect, the invention relates to a method of determining, in a sample, the presence and/or amount of pluripotent stem cells, said method comprising the steps of:
(i) providing a sample suspected of containing one or more pluripotent stem cells;

(ii) contacting the sample with a fluorescent compound disclosed herein under conditions that allow binding of said fluorescent compound to the pluripotent stem cells; and (iii) determining the presence and/or amount of the pluripotent stem cells by measuring the fluorescence of the cells following said contacting.

The term "determine" refers to any qualitative and/or quantitative identification of a subject of interest. "Determining the amount", as used herein, includes determining the number, such as the absolute number, of pluripotent stem cells in a sample.

The term "sample" as used herein refers to a biological sample, or a sample that comprises at least some biological materials such as cells. The samples of this disclosure may be any samples suspected of containing one or more pluripotent stem cells or cells undergoing reprogramming to become induced pluripotent stem cells, including solid tissue samples, such as bone marrow, and liquid samples, such as cell cultures, whole blood, blood serum, blood plasma, cerebrospinal fluid, central spinal fluid, lymph fluid, cystic fluid, sputum, stool, pleural effusion, mucus, pleural fluid, ascitic fluid, amniotic fluid, peritoneal fluid, saliva, bronchial washes and urine. In some embodiments, the sample is a cell culture grown in vitro. For example, the culture may comprise cells cultured in a culture plate or dish, a suspension of cells, or a 3D culture on microcarriers or in scaffolds. The sample may include a mixed cell population.

The term "pluripotent stem cells" as used herein refers to self-renewing cells that can differentiate into endoderm, ectoderm, and mesoderm cells. Pluripotency is also evidenced by the expression of embryonic stem (ES) cell markers. Pluripotent stem cells include, without limitation, embryonic stem cells, induced pluripotent stem cells, and embryonic germ cells. In various embodiments, the pluripotent stem cells are embryonic stem cells or induced pluripotent stem cells.

Embryonic stem cells originate from the inner cell masses of early embryos, and are capable of self-renewal, maintaining pluripotency, and differentiating into cells of three germ layers.

Induced pluripotent stem cells are one type of pluripotent stem cells artificially derived from reprogramming of non-pluripotent cells (e.g., somatic cells) by, for example, introduction of stem cell pluripotency factors, the key factors in maintaining stem cell pluripotency. Somatic cells can be reprogrammed to stem cells by introducing these factors into the somatic cells. Many factors have been reported to have an ability to induce the reprogramming of somatic cells. Preferably, the pluripotency factor(s) is/are one or more selected from the group consisting of Oct4, Sox2 (or Sox1), Klf4 (or Klf2 or KLF5), Nanog, c-Myc (or L-Myc or N-Myc), Lin28 and Esrrb. Said stem cell pluripotency factors may be derived from any desired species.

The term "reprogramming" as used herein refers to a process that reverses the developmental potential of a cell or population of cells (e.g., a somatic cell). Stated another way, reprogramming refers to a process of driving a cell to a state with higher developmental potential, i.e., backwards to a less differentiated state. The cell to be reprogrammed can be either partially or terminally differentiated prior to reprogramming. In the context of the present application, reprogramming encompasses a complete reversion of the differentiation state, i.e., an increase in the developmental potential of a cell to that of a cell having a pluripotent state. In some embodiments, reprogramming encompasses driving a somatic cell to a pluripotent state, such that the cell has the developmental potential of a pluripotent stem cell. In some embodiments, reprogramming encompasses driving an adult stem cell to a pluripotent state, such that the cell has the developmental potential of a pluripotent stem cell.

In general, it has been accepted in the art that the induced pluripotent stem cells are equivalent to embryonic stem cells, given that the induced pluripotent stem cells have the characteristics of: (a) stem cell gene and protein expression; (b) chromosome methylation; (c) doubling time; (d) embryo formation; (e) teratoma formation; (f) viable chimera formation; (g) hybridoma; and (h) differentiation.

The samples and/or the cells disclosed herein may be obtained from any organism, including mammals such as humans, primates (e.g., monkeys, chimpanzees, orangutans, and gorillas), cats, dogs, rabbits, farm animals (e.g., cows, horses, goats, sheep, pigs), and rodents (e.g., mice, rats, hamsters, and guinea pigs), preferably from humans. The organism may be a healthy organism or suffer from a disease condition. Disease conditions may include any disease, such as cancer, diabetes, metabolic syndrome, or an autoimmune disorder.

In accordance with the present invention, a sample suspected of containing pluripotent stem cells is provided, and the pluripotent stem cells comprised in the sample are contacted with and consequently specifically labelled by a fluorescent compound disclosed herein, enabling the subsequent detection and/or measurement of the labelled cells.

In various embodiments, step (ii) does not comprise a washing step following said contacting.

By virtue of the selectivity of the fluorescent compounds for pluripotent stem cells, following the labeling of step (iii), an additional step of removing unbound fluorescent labels may be disposed of.

In various embodiments, the method further comprises a step of:

(iv) isolating the pluripotent stem cells labelled by the fluorescent compound from the sample.

The compounds disclosed herein, BDL-E5 for example, are not toxic, rendering them suitable for use in isolating labeled living cells from those that are not labeled.

In various embodiments, the labelled cells are isolated by fluorescence-activated cell sorting (FACS).

It should be noted that the fluorescent compounds disclosed herein may, in the context of the present application, be used in combination with one or more other detectable labels (e.g. a fluorescently labeled antibody against a cell surface marker and/or a vitality stain such as propidium iodide), such that a plurality of parameters could be determined simultaneously for reliable analysis and/or isolation of the target cells.

It is postulated that tumor-initiating cells (also known as cancer stem cells), which reportedly possess some properties of pluripotent stem cells, may also be specifically stained by the compounds of this disclosure such as BDL-E5. The identification, characterization, and/or isolation of tumor-initiating cells by said compounds are therefore also contemplated to be within the scope of the present invention.

In a third aspect, the invention relates to a method of determining, in a sample, the presence and/or amount of cells undergoing reprogramming to become induced pluripotent stem cells, said method comprising the steps of:

(i) providing a sample suspected of containing one or more cells undergoing reprogramming to become induced pluripotent stem cells;

(ii) contacting the sample with a fluorescent compound disclosed herein under conditions that allow binding of said fluorescent compound to the cells undergoing reprogramming to become induced pluripotent stem cells; and (iii) determining the presence and/or amount of the cells undergoing reprogramming to become induced pluripotent stem cells by measuring the fluorescence of the cells following said contacting.

Without wishing to be bound to any theory, it is believed that the fluorescent compounds disclosed herein specifically bind to not only pluripotent stem cells but also cells undergoing reprogramming that have been determined to become induced pluripotent stem cells, even at an early stage of the reprogramming.

For example, the inventors surprisingly found that the fluorescent compound BDL-E5 specifically stains early reprogramming cells, but not somatic cells or adult stem cells such as ASCs or DPSCs. In addition, as detailed below, BDL-E5 allows early detection and enrichment of reprogramming cells, as early as seven days before stem cell colonies are visible. Consistently, BDL-E5$^+$ reprogrammed cells exhibit high expression levels of pluripotent genes, some of which are nearly comparable to those in mature induced pluripotent stem cells. BDL-E5 therefore offers a valuable tool for detecting authentic early reprogramming cells, allows enrichment of the reprogramming-ready cell population, and helps uncover novel regulators of reprogramming.

In various embodiments, the cells undergoing reprogramming to become induced pluripotent stem cells are mammalian cells, preferably human, mouse, or rat cells, more preferably human cells.

In various embodiments, step (ii) does not comprise a washing step following said contacting.

As shown in the Examples of the present application, CDy1 presented higher signals toward human reprogramming cells but also higher background staining against non-reprogramming cells, but BDL-E5, an exemplary compound of those disclosed herein, exhibited low non-specific staining against non-reprogramming cells and therefore, unlike CDy1, does not require washing after the staining process to reduce background signals.

In various embodiments, the method further comprises a step of:

(iv) isolating the cells undergoing reprogramming to become induced pluripotent stem cells labelled by the fluorescent compound from the sample.

In various embodiments, the labelled cells are isolated by fluorescence-activated cell sorting (FACS).

Following isolation, the enriched cells are believed to exhibit properties of pluripotent stem cells, such as colony formation in vitro and teratoma formation in vivo in immunocompromised recipient animals.

One skilled in the art would readily appreciate that the method disclosed herein could also be used to identify agents that inhibit or stimulate cell reprogramming.

In a fourth aspect, the invention relates to the use of the fluorescent compound disclosed herein in the detection and/or isolation of pluripotent stem cells.

In another aspect, the invention relates to the use of the fluorescent compound disclosed herein in the detection and/or isolation of cells undergoing reprogramming to become induced pluripotent stem cells.

The present invention is further illustrated by the following examples. However, it should be understood, that the invention is not limited to the exemplified embodiments.

EXAMPLES

Materials and Methods

Isolation of ASCs

WAT was isolated from subcutaneous (abdominal region) and visceral (omental region) depots from 2 human volunteers (S15-S16, undergoing bariatric surgery, with approval by the National Healthcare Group Domain Specific Review Board at National Healthcare Group, Singapore) as described previously (Ong, et al. (2014). Stem Cell Reports 2, 171-179; Takeda, et al. (2016). Diabetes 65, 1164-1178). S15 is a 24-year old Indian female and S16 is a 36-year old Indian male. ASCs were isolated from WAT and cultured, as previously described (Sugii, et al. (2011). Nature Protoc 6, 346-358). Cells only up to passage 5 were used for experiments. MSC cell surface markers and multipotency of ASCs used herein were confirmed by flow cytometry and differentiation assays, respectively (Ong, et al. (2014). Stem Cell Reports 2, 171-179).

ASC and DPSC Culture

Different lines of ASCs and DPSCs were obtained from commercial sources (Lonza, Invitrogen and PromoCell). ASCs were cultured in DMEM containing 15% FBS, NEAA (1%), basic FGF (bFGF; 5 ng/ml) and Pen/Strep as previously described (Ong, et al. (2014). Stem Cell Reports 2, 171-179; Takeda, et al. (2016). Diabetes 65, 1164-1178; Sugii, et al. (2011). Nature Protoc 6, 346-358), and DPSCs were grown in vitro in Poietics™ DPSC BulletKit medium (Lonza) according to manufacturer's instructions. Media change for the cells was performed every 2-3 days. All cells were cultured in a humidified incubator at 37° C. in 5% $CO_2$.

iPS Reprogramming Using Episomal Vectors

Episomal plasmids developed by Yamanaka's lab were obtained from Addgene: pCXLEhOct3/4-shp53-F (Addgene #27077), pCXLE-hSK (Addgene #27078), pCXLE-hUL (Addgene #27080) and pCXLE-EGFP (Addgene #27082) (Okita, et al. (2011). Nat Methods 8, 409-412). $1 \times 10^6$ cells were suspended together with 1 μg of each episomal vector in Nucleofector solution supplied in the Nucleofector Kit R (Lonza). Then the cells were transfected with the Program FF-113 on a Nucleofector 2b Device. The transfected cells were then cultured in ASC or DPSC medium (MSC medium) supplemented with 0.5 mM sodium butyrate, with daily media change. On Day 7 dpn, $1 \times 10^5$ viable cells were seeded over MEF feeders (GlobalStem) into one well of a 6-well plate for feeder-based iPS derivation; $2 \times 10^5$ viable cells were seeded for feeder-free iPS derivation into one well of a 6-well plate pre-coated with Matrigel (Corning). The next day, MSC medium was changed to feeder-based hES medium (DMEM/F12 supplemented with 20% knock out serum replacement, 1% GlutaMAX, 1% NEAA, Pen/Strep, 0.1 mM β-mercaptoethanol and 10 ng/ml b-FGF) or to feeder-free mTeSR1 (StemCell Technologies), supplemented with sodium butyrate. At 12 dpn, supplementation of sodium butyrate was stopped, and conditioned further with SMC4 cocktail (consisting of small molecules: PD0325901, CHIR99021, Thiazovivin, and SB431542 (FOCUS Biomolecules)) in hES medium/mTeSR1. This media supplement was continued until initial colony formation began.

Fluorescent Probes and Screening

The chemical properties of the BDL library are previously described (Jeong et al., 2015). BDL-E5 is based on 4,4-difluoro-4-bora-3a,4a-diaza-s-indacene (BODIPY), with calculated mass of 528.3 and absorption maximum/emission maximum of 578/599 nm. Primary, secondary and tertiary screening of fluorescent probes on AiPS, ASCs, DiPS and DPSCs were performed as described previously (Im, et al. (2010). Angew Chem Int Ed Engl 49, 7497-7500; Kang, et al. (2011). Nat Protoc 6, 1044-1052) and in the Results section. Unless described otherwise, BDL-E5 and CDy1 images were acquired by the Tetramethylrhodamine (TRITC) channel of ImageXpress Micro High-Content Imaging System, which had the Adaptive Background Correction function enabled.

Immunofluorescence Live Cell Staining

Reprogrammed cells were immune-stained with fluorescent live cell stain TRA-1-60 (R&D Systems, GloLIVE NL557) as per manufacturer's instructions. After incubating with the live staining antibodies for 30 min and Hoechst 33342 for 10 min, cells were washed 3 times with PBS and images with the Cy5 and DAPI channels, respectively, were immediately captured.

Fluorescent Activated Cell Sorting (FACS)

Reprogrammed ASCs and DPSCs, AiPS and DiPS on D7 or D14 dpn were stained with BDL-E5 for 1 hour and then harvested using TrypLE and resuspended in 1×PBS. The cells were then subjected to FACS in the MoFlo XDP Cell Sorter (Beckman Coulter) under sterile conditions.

RNA Sequencing

At 7 dpn, reprogrammed DPSC2 cells were stained with BDL-E5 and harvested for FACS as mentioned above. 20-30 BDL-E5$^+$ and BDL-E5$^-$ cells were collected in 100 µl of 1×PBS; single-cells of DiPS and DPSCs were also passed through the Cell Sorter and collected for RNA isolation. RNA was isolated from single cells and cDNA preparation, amplification and quantification were as described in the Supplementary Methods section. Library preparation and sequencing was done by sequencing platform at Genome Institute of Singapore. Paired-end RNA sequencing reads were aligned to the human genome (hg19) using TopHat2-2.0.12 (Kim, et al. (2013). Genome Biol 14, R36) (default parameter). Transcript abundances at both the gene and isoform levels were estimated by cufflinks-2.2.0 (Trapnell, et al. (2010). Nat Biotechnol 28, 511-515) and the expression was reported as fragments per kilobase of exon per million fragments mapped (FPKM).

Real-Time PCR

Total RNA was extracted using TRIzol reagent (Invitrogen) and cDNA conversion was made by the RevertAid H minus first strand cDNA synthesis kit (Fermentas) as per manufacturer's instructions. qPCR was performed using SYBR Green PCR Master Mix on a StepOnePlus Real-Time PCR System (Applied Biosystems) using the primer pairs shown in Table 1. Relative mRNA was calculated and normalized to the level of GAPDH.

TABLE 1 qPCR primers

| Gene | Forward primer | SEQ ID NO: | Reverse primer | SEQ ID NO: |
|---|---|---|---|---|
| GAPDH | CAAGGTCATCCATGACAACTTTG | 1 | GGCCATCCACAGTCTTCTGG | 2 |
| Activin A | CTCGGAGATCATCACGTTTG | 3 | CCTTGGAAATCTCGAAGTGC | 4 |
| Lin28 | GAAGCGCAGATCAAAAGGAG | 5 | GCTGATGCTCTGGCAGAAGT | 6 |
| Nanog | CCAACATCCTGAACCTCAGC | 7 | GCTATTCTTCGGCCAGTTG | 8 |
| DPPA2 | TGGTGTCAACAACTCGGTTTG | 9 | CTCGAACATCGCTGTAATCTGG | 10 |
| TGF-β1 | GCAGCACGTGGAGCTGTA | 11 | CAGCCGGTTGCTGAGGTA | 12 |
| FN1 | CTGGCCGAAAATACATTGTAAA | 13 | CCACAGTCGGGTCAGGAG | 14 |
| DNMT3B | TACACAGACGTGTCCAACATGGGC | 15 | GGATGCCTTCAGGAATCACACCTC | 16 |
| GDF3 | AAATGTTTGTGTTGCGGTCA | 17 | TCTGGCACAGGTGTCTTCAG | 18 |
| Cdh1 | GAAGGTGACAGAGCCTCTGGAT | 19 | GATCGGTTACCGTGATCAAAATC | 20 |
| EpCAM1 | TGTGTGCGTGGGA | 21 | TTCAAGATTGGTAAAGCCAGT | 22 |
| ZEB1 | AGCAGTGAAAGAGAAGGGAATGC | 23 | GGTCCTCTTCAGGTGCCTCAG | 24 |
| ZEB2 | CGCAGCACATGAATCACAGG | 25 | CGTATCGTTTCGGGATCCGT | 26 |
| Snail1 | TCTGAGGCCAAGGATCTCCA | 27 | CATTCGGGAGAAGGTCCGAG | 28 |
| Snail2 | TCATCTTTGGGGCGAGTGAG | 29 | TCCTTGAAGCAACCAGGGTC | 30 |
| CREB1 | ATTGGAAGGAAAGGGGAGGG | 31 | GGCTTGAACACATCTTGGCA | 32 |
| PRKAB2 | CAGTAGAGTGGGGCAGGAAA | 33 | TCCCATTTCACATCTGGGCT | 34 |
| GATA2 | AAGGCTCGTTCCTGTTCAGA | 35 | GGCATTGCACAGGTAGTGG | 36 |
| SOX7 | GAGCAGTGTGGACACGTACC | 37 | GTCCAGGGGAGACATTTCAG | 38 |
| SMA | CTGTTCCAGCCATCCTTCAT | 39 | TCATGATGCTGTTGTAGGTGGT | 40 |
| AFP | AAGAATTTCAGCATGATTTTCCA | 41 | CACCCACTTCATGGTTGCTA | 42 |

CREB1 Overexpression and Silencing by siRNA

CREB1 was overexpressed in ASCs and DPSCs during reprogramming using the commercially available CREB1 Human cDNA ORF clone (Origene) according to manufacturer's instructions. Knockdown of CREB1 was achieved using the ON-TARGETplus Human CREB1 siRNA—SmartPool (GE Dharmacon) according to manufacturer's instructions. DPSCs and ASCs were either nucleofected with the CREB1 OE along with the episomal reprogramming factors for overexpression of CREB1 during reprogramming, or transfected with siCREB1 and then nucleofected with the episomal reprogramming factors for silencing of CREB1 during reprogramming.

Generation of Embryoid Bodies and 3-Germ Layer Immunocytochemistry

For spontaneous in vitro differentiation, DPSC-derived iPS (DiPS) cells were grown to confluency. Using dispase, the cells were resuspended in medium containing DMEM-F12 supplemented with 10% Knockout Serum Replacement (KOSR), 1% Non-Essential Amino Acid (NEAA) and 1% Glutamax. These cells were transferred to low attachment 6-well plates (Greiner Bio One). Media change was made every 3 days. Embryoid bodies (EBs) were formed as previously described (Kurosawa H (2007). J Biosci Bioeng 103 (5):389-398), day 8-10 EBs were transferred to a 12-well plate precoated with 0.1% gelatin and cultured further for 12 more days. Subsequently, the attached EBs were allowed to undergo spontaneous differentiation. These differentiated cells were later stained with 3 Germ Layer Immunocytochemistry antibodies (Life Technologies) as per the manufacturer's instructions.

Generating and Culturing of Reprogrammed Cells on Cytodex 3 Microcarriers

Reprogrammed monolayer ASCs and DPSCs were dissociated into single cell suspension using Dispase. Single cell suspension was transferred into a 6-well Suspension Culture Plate (Greiner bio-one) with Matrigel (Geltrex™, ThermoFisher)-coated Cytodex 3 microcarrier in 4 ml of mTeSR1 supplemented with 10 µM of Rock Inhibitor Y27632 (Calbiochem). The plate was placed on an orbital shaker (110 rpm) for at least 2 hours for cell attachment. Afterward, the plate was transferred to static condition and incubated at 37° C./5% $CO_2$. Media change was carried out with mTeSR1 daily thereafter by aspirating 4 ml of spent medium from the well and adding 4 ml of fresh media (80% medium exchange). On Day 7, the cells on microcarriers were supplemented and maintained with 4 ml of mTeSR1+ SMC4 media. 80% medium change was carried out every day.

Fluorescent Probe Staining on Microcarriers

BDL-E5 probe staining of reprogrammed ASCs and DPSCs on microcarriers was carried out on Day 14 and 21 dpn. The microcarrier culture was washed twice with sterile D-PBS. Prior to staining, media was changed to mTeSR1 with 500 nM BDL-E5 probe and Alexa Fluor® 488 Mouse anti-human TRA-1-60 (200× dilution) (BD Pharmingen™). Cultures were incubated for 1 hour. The cells were then washed twice with D-PBS and replaced with mTeSR1 prior to imaging. Images were taken using Axio Observer Fluorescent Microscope (Carl Zeiss).

Fluorescent Subcellular Organelle Staining

Reprogrammed DPSCs at 7 dpn on MG were stained for cell organelle marker dyes (Molecular Probes) for endoplasmic reticulum (ER) (ER-Tracker™ Green (BODIPY® FL Glibenclamide)), Golgi complex (BODIPY® FL C5-Ceramide (N-(4,4-Difluoro-5,7-Dimethyl-4-Bora-3a,4a-Diazas-Indacene-3-Pentanoyl)Sphingosine)), lysosome (LysoTracker® Green DND-26), or mitochondria (MitoTracker® Green FM). Confocal images were taken to visualize the staining.

iPS Reprogramming Using Viral Methods iPS cells were also generated from DPSCs with the traditional protocol involving retroviral vectors expressing OCT4, SOX2, KLF4, and C-MYC (Sugii, et al. (2011). Nature Protoc 6 (3):346-358). BJ human neonatal fibroblasts were reprogrammed using lentiviral OCT4, SOX2, KLF4, and C-MYC as described previously (Toh, et al. (2016). Cell Rep 15 (12):2597-2607).

Single Cell RNA Isolation for RNA Sequencing

Prepared Mix A (Lysis), Mix B (RT) and Mix C (PreAmp)

| Mix A | vol (ul) |
| --- | --- |
| C1-loading reagent | 1 |
| Water | 3 |
| Lysis Buffer (0.2% triton-X100 in H2O) | 12 |
| oligo dT (20 uM) | 3.5 |
| rnase inhitor (40 U/ul) | 0.5 |
| total volume | 20 |

| Mix B | Vol (ul) |
| --- | --- |
| Water | 1.692 |
| 5X-Strand buffer | 5.6 |
| DTT (100 mM) | 1.4 |
| dNTP | 2.8 |
| TSO (50 uM) | 0.672 |
| rnase inhibitor (40 U/ul) | 0.7 |
| RT enzyme (200 U/ul) | 2.8 |
| MgC12 (0.5M) | 0.336 |
| total volume | 16 |

| Mix C | Vol (ul) |
| --- | --- |
| PCR Water | 39.5 |
| 10X Advantage 2 PCR Buffer | 6 |
| 50X dNTP Mix | 2.4 |
| IS PCR Primer (20 uM) | 1 |
| 50X Advantage 2 Polymerase MN | 2.4 |
| C1 Loading Reagent | 2.7 |
| total volume | 54 |

Dissociated cells into single cell suspension

Aliquoted 2 µl mix A into a 200 µl thin PCR tube.

Added 1 µl single cell suspension into the PCR tube as following.

| Mix A | 2 µL |
| --- | --- |
| Prepared Cells | 1 µL |
| Subtotal | 3 µL |

The lysis step was run by the following program.

| Temperature | Time |
| --- | --- |
| 72° C. | 3 min |
| 4° C. | 10 min |

-continued

| Temperature | Time |
| --- | --- |
| 25° C. | 1 min |
| 4° C. | hold |

Mix B was combined with lysis thermal products from step 4

| lysis thermal products from above | 3 μL |
| --- | --- |
| Mix B | 4 μL |
| sub total | 7 μL |

Following program was run:

| Temperature | Time |
| --- | --- |
| 42° C. | 90 min |
| 70° C. | 10 min |
| 4° C. | hold |

Mix C was combined with RT thermal products from step 6

| PCR Mix C | 4.5 μL | 9.0 μL |
| --- | --- | --- |
| RT Reaction | 0.5 μL | 1.0 μL |
| sub total | 5 μL | 10 μL |

Program was run as follows:

| Temperature and Time | Cycles |
| --- | --- |
| 95° C. 1 min | 1 |
| 95° C. 20 sec | 5 |
| 58° C. 4 min | |
| 68° C. 6 min | |
| 95° C. 20 sec | 9 |
| 64° C. 30 sec | |
| 68° C. 6 min | |
| 95° C. 30 sec | 7 |
| 64° C. 30 sec | |
| 68° C. 7 min | |
| 72° C. 10 min | 1 |
| 4° C. hold | 1 |

Proliferation Assay

To ensure that BDL-E5 was not toxic to the cells, DPSCs were incubated with BDL-E5 (500 nM) for 48 h and 72 h and viable cells were counted in a haemocytometer using the Tryphan Blue method. DPSCs in which CREB1 was over-expressed or silenced were also counted at 72 h post nucleofection to determine if gene manipulation has affected the cell proliferation.

Statistical Analysis

All results are presented as means +/−SEM. Statistical analysis was performed using t-tests (two sided; paired). Differences with p value<0.05 were considered significant.

Example 1: Screening for a Human Pluripotency-Specific Fluorescent Probe

A high-throughput system using in-house Diversity Orientated Fluorescence Library Approach (DOFLA) was employed to screen 46 fluorescent probes that the inventors predicted may specifically recognize pluripotent stem cells. To identify fluorescent probes that detected human pluripotent stem cells, ASCs, ASC-derived iPS (AiPS) cells, DPSCs, and DPSC-derived iPS (DiPS) cells were used. ASCs and DPSCs were chosen as these cells show relatively high reprogramming efficiencies and were previously shown to exhibit many of the conventional pluripotent markers, thus serving as stringent negative controls for authentic pluripotent stem cells. Cells were seeded onto 384-well plates (primary screen) or 96-well plates (secondary and tertiary screen) coated with mouse embryonic fibroblasts (MEF) or matrigel (MG) for DOFLA screening (FIG. 1A). After 48 h, cells were stained with library probes (500 nM) for 1 h. Fluorescence was imaged using the ImageXpress System under the following conditions: "No wash" (after 1 h probe incubation), "Wash 0 min" (after one wash with PBS), "Wash 60 min" (after wash and destain for 1 h) and "Wash 180 min" (after wash and destain for 3 h) (FIG. 1A).

Figure 2:
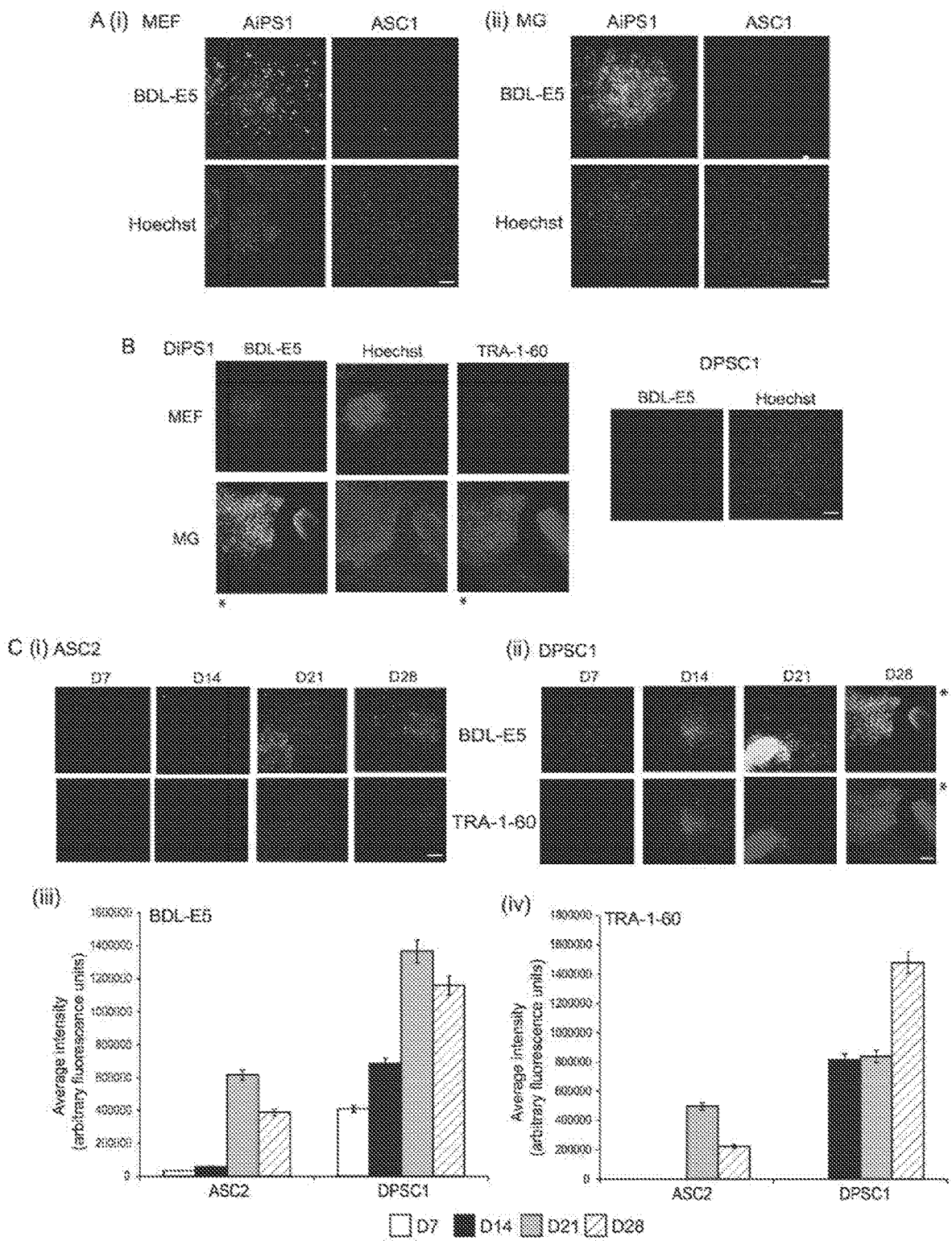
FIG. 2: (A) Fluorescent images (10× objective) of BDL-E5 probe (No wash) and Hoechst 33342 staining of AiPS1 colonies and its original ASC1 (ASC line #1) on MEF-(i) and MG-coated (ii) plates from primary screening (n=3). (B) Fluorescent images (10×) of BDL-E5 probe (No wash), Hoechst and TRA-1-60 on DiPS1 colonies and DPSC1 (DPSC line #1) on MEF- and MG-coated plates from secondary screening (n=3). (C) Fluorescent images (10×) and average fluorescence intensity of BDL-E5 probe (No wash) and TRA-1-60 on ASC2 (i), (iii) and DPSC1 (ii), (iv) on MG-coated plates at 7, 14, 21, 28 days post nucleofection (dpn) with reprogramming factors. *Represents the same images. Cells were incubated with 500 nM of BDL-E5 in appropriate media for 1 h (n=3). Scale bar represents 100 µm.
Figure 8:
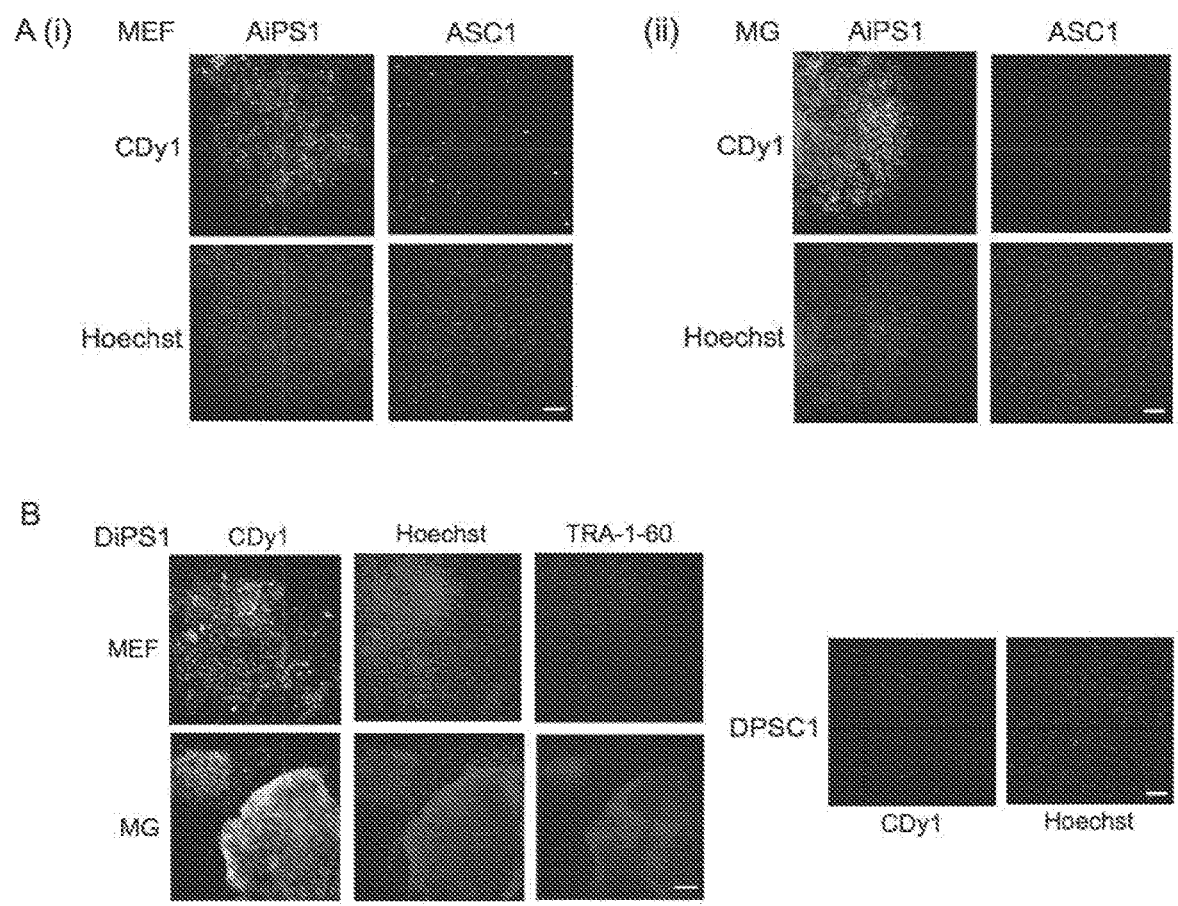
FIG. 8: (A) Fluorescent images (10× objective) of CDy1 probe (Wash 180 min) and Hoechst on AiPS1 colonies and ASC1 on (i) MEF- and (ii) MG-coated plates from primary screening (n=3). (B) Fluorescent images (10×) of CDy1 probe (Wash 180 min), Hoechst and TRA-1-60 on DiPS1 colonies and DPSC1 on MEF- and MG-coated plates from secondary screening. Cells were incubated with 500 nM of CDy1 in appropriate media for 1 h (n=3). Scale bar represents 100 µm.

Images were analyzed using the MetaXpress Image Acquisition and Analysis software. Following tertiary screening, two probes were shortlisted to develop further as pluripotent probes: BDL-E5 and CDy1. The chemical structure of BDL-E5 is depicted in FIG. 1B. These two probes showed significantly increased intensity of fluorescence in human iPS cells compared with their original somatic cells and MEFs. FIG. 2A shows increased BDL-E5 staining (No wash) in AiPS colonies grown on MEF- or MG-coated plates, compared with their original somatic cells from the primary screening. FIG. 8 shows increased CDy1 staining in AiPS cells on MEF- or MG-coated plates compared with ASCs from the primary screen.

Secondary screening was performed to confirm that the probes selectively stained different iPS colonies. FIG. 2B showed significantly increased fluorescence intensity of BDL-E5 staining (No wash) in DiPS colonies grown on MEF- or MG-coated plates compared with original DPSCs. The BDL-E5$^+$ colonies were also positively stained for the pluripotency marker TRA-1-60. FIG. 8B showed increased staining of CDy1 and TRA-1-60 positive staining in DiPS colonies grown on MEF- or MG-coated plates compared with DPSCs from the secondary screening. Different classes of probes were shown to highlight human iPS cells in both feeder and feeder-free conditions. These results also confirm applicability of CDy1 to human cells.

Figure 9:
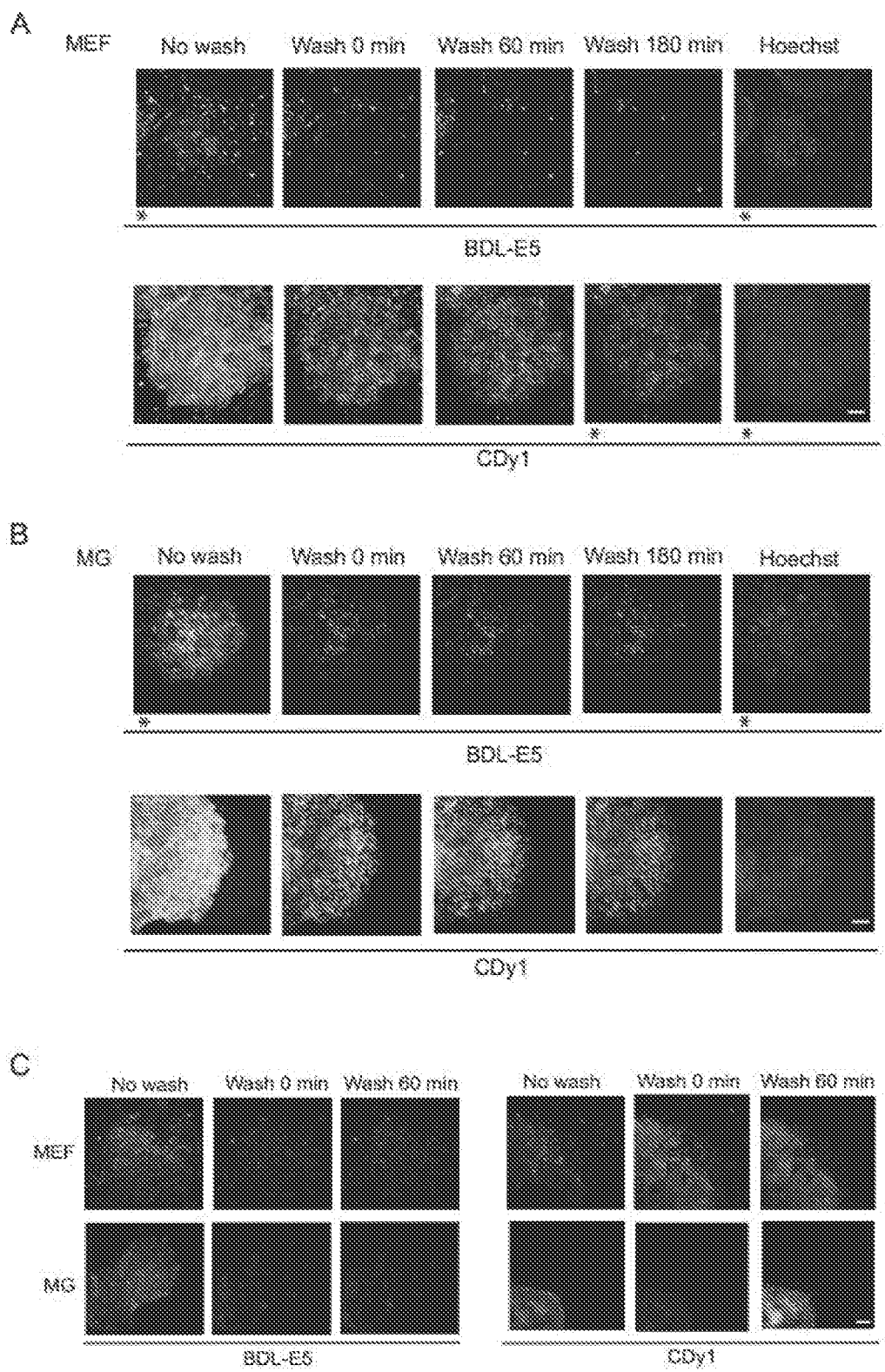
FIG. 9: (A, B) Fluorescent images (10×) of BDL-E5, CDy1 and Hoechst on AiPS1 colonies on MEF- and MG-coated plates at different conditions (No wash, Wash 0 min, Wash 60 min, Wash 180 min) after incubation with 500 nM probe for 1 h (n=3). *Represents the same images that are presented in FIGS. 2 and 8. (C) Fluorescent images (10×) of BDL-E5 and CDy1 on AiPS3 colonies on MEF- and MG-coated plates at different conditions (No wash, Wash 0 min, Wash 60 min) after incubation with 500 nM probe for 1 h (n=3). Scale bar represents 100 µm.

Example 2: BDL-E5 Identified as a Live Fluorescent Probe that Detects Pluripotent Stem Cells Based on the primary and secondary screenings for live fluorescent probes that can specifically identify pluripotent cells, BDL-E5 and CDy1 were chosen as two probes to further analyze. Tertiary screening was performed using the two probes on AiPS colonies under the following probe staining conditions: No wash, Wash 0 min, Wash 60 min, and Wash 180 min. As shown in FIG. 9A, when AiPS colonies were grown on MEF-coated plates, BDL-E5 staining was greatest with regard to the signal-to-background ratio under No wash conditions, and CDy1 staining was greatest under Wash 60 min or Wash 180 min conditions. When AiPS colonies were grown on MG-coated plates (FIG. 9B), BDL-E5 staining was greatest under No wash conditions, and CDy1 staining was greatest under Wash 60 min or Wash 180 min conditions. Similar results were also obtained with different subject-derived AiPS colonies, as shown in FIG. 9C.

Example 3: BDL-E5 can Identify Early Reprogramming Cells

After combining all the results from the primary, secondary, and tertiary screening, the BDL-E5 probe was chosen as the best probe amongst the screened probes, as it did not require washing (thus was less time- and labor-intensive). Further experiments were carried out using BDL-E5. To determine whether BDL-E5 identifies the early stages of pluripotency, ASCs and DPSCs were reprogrammed using nucleofection of episomal vectors, and seeded onto MG-coated plates (feeder-free, viral-free reprogramming method). BDL-E5 staining was performed on reprogramming cells at 7, 14, 21 and 28 days post nucleofection (dpn). As shown in FIG. 2C (i) and (ii), the intensity of the fluorescence of BDL-E5 staining increased with increasing time as iPS colonies were formed from ASCs or DPSCs. TRA-1-60 staining further confirmed that cells that stained positive for BDL-E5 were pluripotent. Quantitative data confirmed this staining as shown in FIG. 2C (iii) and (iv). Interestingly, BDL-E5-positive cells appeared well before colonies were visible and stained positively for TRA-1-60. BDL-E5-positive cells were found around 14 dpn (as opposed to 21 dpn for TRA-1-60-positive colonies) in reprogramming ASCs, while they were observed as early as 7 dpn (as opposed to 14 dpn for TRA-1-60) in reprogramming DPSCs.

Figure 3:
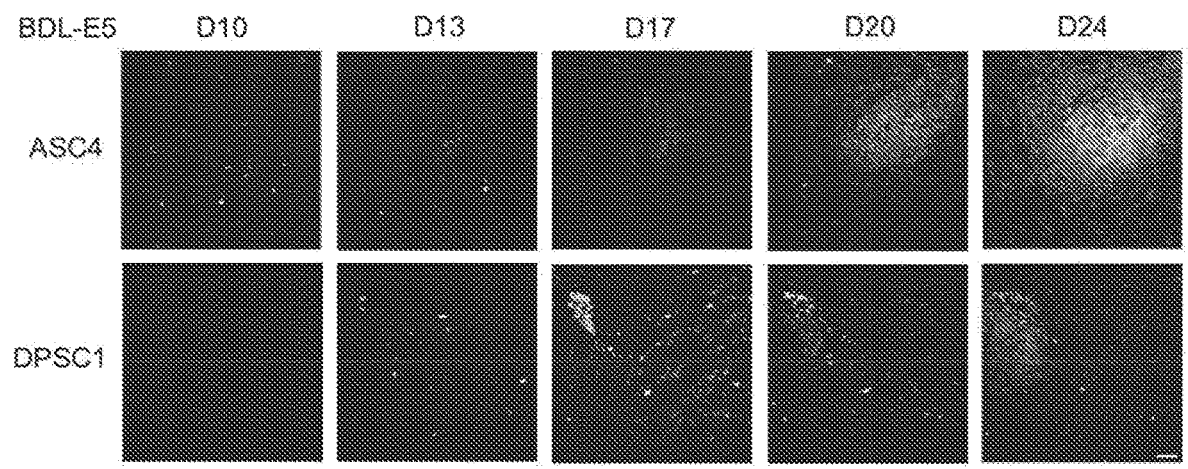
FIG. 3: Images showing BDL-E5 staining tracked daily on reprogrammed cells of ASC4 and DPSC1 on MG. Representative images (10×) were taken at 10, 13, 17, 20 and 24 dpn (n=3). Scale bar represents 100 µm.

To confirm that BDL-E5 specifically stains authentic reprogramming cells that eventually form colonies, ASCs and DPSCs were reprogrammed using the same episomal, feeder-free method. BDL-E5 staining was performed as described previously on the reprogrammed cells every 48 h and images were taken from the same field of view daily until iPS colonies formed. FIG. 3 shows representative images at 10, 13, 17, 20, and 24 dpn for reprogrammed ASCs and DPSCs. It is clear that only cells staining positive for BDL-E5 formed iPS colonies.

Figure 4:
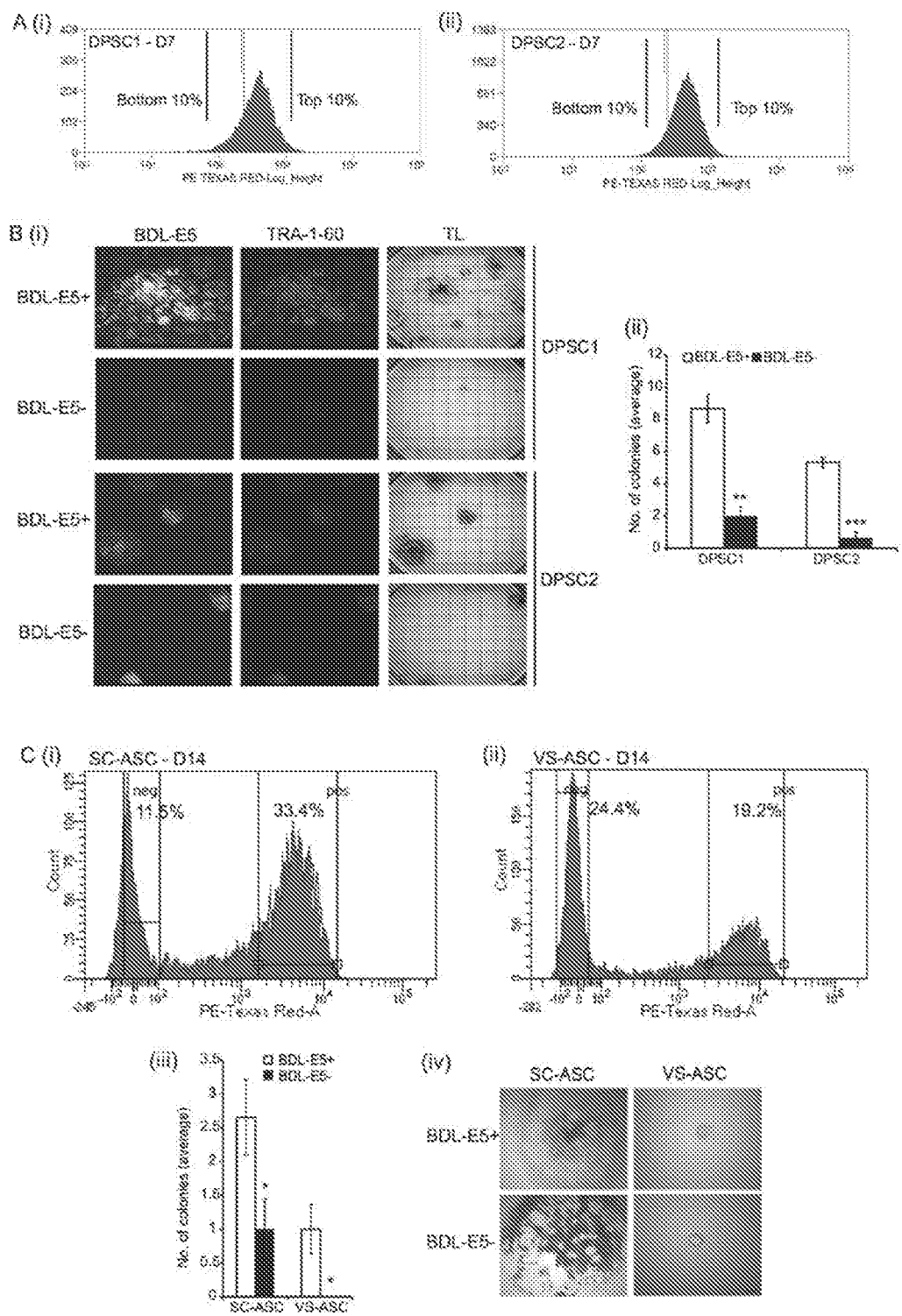
FIG. 4: (A) Histogram (FACS) showing BDL-E5$^+$ cell populations at 7 dpn: DPSC1 (i) and DPSC2 (ii). Relative cell count is indicated on the y-axis, and fluorescence intensity (Texas Red channel) on the x-axis. The top 10% and bottom 10% of cell populations are as indicated (n=3). (B) (i) Fluorescent images of BDL-E5, TRA-1-60 and transmitted light (TL) images (4×) showing iPS colonies derived from BDL-E5$^+$ and BDL-E5$^-$ cell populations of DPSC1 and DPSC2 following FACS at 7 dpn. (ii) Graph showing average number of DiPS colonies in reprogrammed BDL-E5$^+$ and BDL-E5$^-$ cell populations obtained after FACS of DPSC1 and DPSC2. p<0.01 and *p<0.001 denote statistical significance (n=3). (C) Histogram showing FACS of BDL-E5$^+$ and BDL-E5$^-$ cell populations at 14 dpn from SC-ASC S15 (i) and VS-ASC S15 (ii). The percentage of positively and negatively stained cells is shown. (iii) Graph showing average number of iPS colonies in BDL-E5$^+$ and BDL-E5$^-$ cell populations obtained after FACS at 14 dpn from SC-ASC S15 and VS-ASC S15. *p<0.05 denotes statistical significance. (iv) TL images (10×) showing iPS colonies from SC-ASC S15 and VS-ASC S15 following FACS for BDL-E5$^+$ and BDL-E5$^-$ cell populations. Similar results were obtained with S16-derived SC-ASC and VS-ASC (n=3). Scale bar represents 100 µm.
Figure 5:
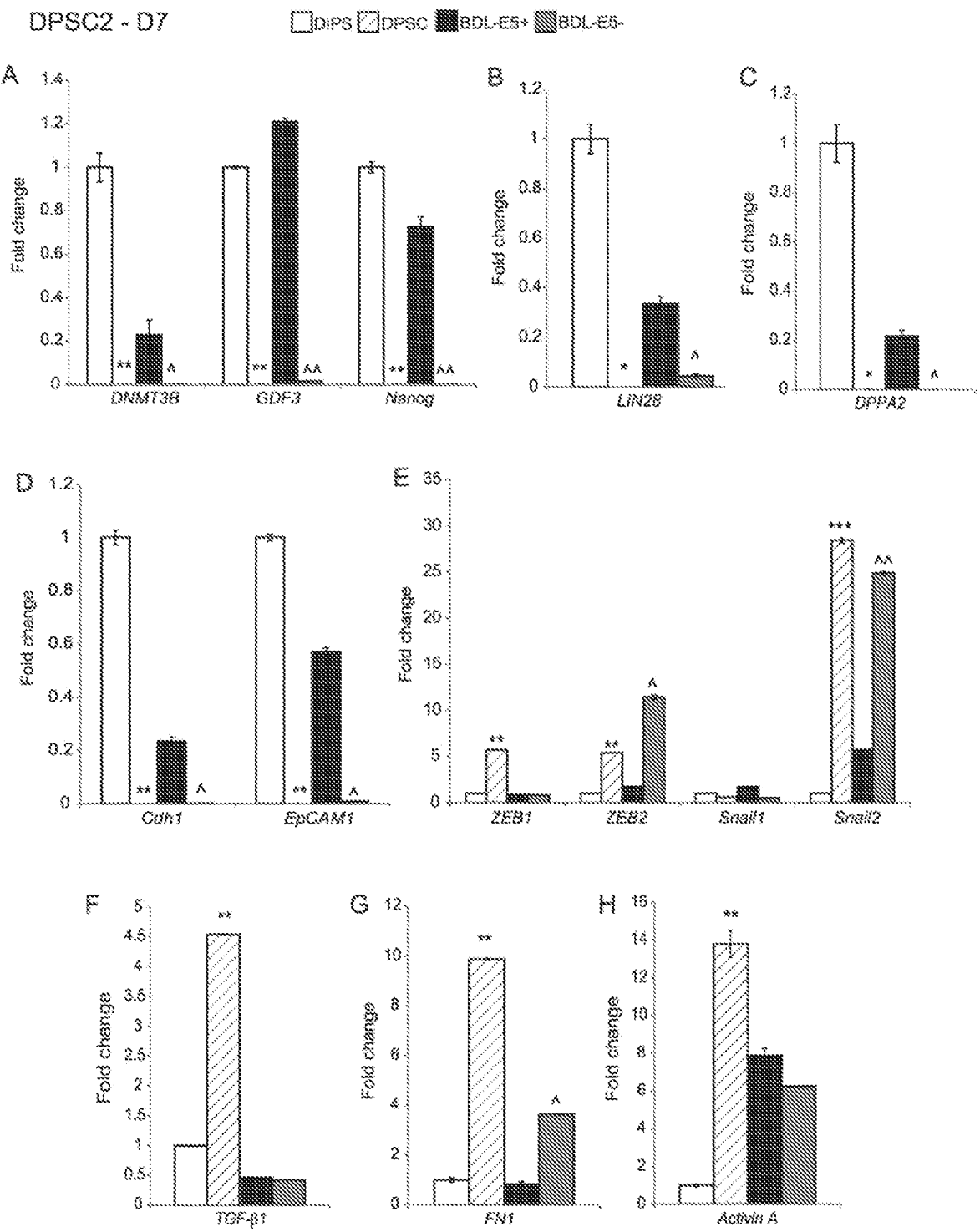
FIG. 5: Representative graphs showing gene expression of DNMT3B, GDF3, and Nanog (A); LIN28 (B); DPPA2 (C); Cdh1, and EpCAM1 (D); ZEB1, ZEB2, Snail1, and Snail2 (E); TGF-β1 (F), FN1 (G); and Activin A (H) in RNA isolated from DiPS2, DPSC2, BDL-E5$^+$, and BDL-E5$^-$ cells of DPSC2 obtained after FACS at 7 dpn (n=3). DiPS2 colonies were generated from the original DPSC2 cells that were similarly subjected to FACS. *p<0.05 and **p<0.01 denote significance compared with DiPS2; ^p<0.05 and ^^p<0.01 denote significance compared with BDL-E5$^+$.

Example 4: BDL-E5+ Reprogrammed Cells Generate Higher Quantity and Quality of Ips Cells Different DPSC cell lines were reprogrammed using the feeder-free episomal method, incubated with BDL-E5, and subjected to fluorescence activated cell sorting (FACS) at 7 dpn. As shown in FIG. 4A, the bottom 10% and top 10% of cells stained with BDL-E5 were sorted, collected, and seeded onto MEF-coated plates. FIG. 10A (i) and (ii) represents the unstained DPSCs. The cells were allowed to grow for the next two weeks until colonies appeared. BDL-E5+ (top 10%, positively stained) cells gave rise to an increased number of iPSCs, while BDL-E5− (bottom 10%, negatively stained) cells gave rise to significantly fewer colonies per well (FIG. 4B).

Next, the inventors investigated whether the probe was useful in assisting reprogramming selection of obese patient-derived ASCs from subcutaneous (SC) and visceral (VS) fat depots. Unlike SC-derived ASCs, VS-derived ASCs exhibit cellular defects, including adipogenesis (Ong et al., 2014; Takeda et al., 2016). It was found that VS-ASCs also showed substantial defects in reprogramming, typically resulting in <1 colony being formed per well. Interestingly, when ASCs were subjected to FACS with BDL-E5 at 14 dpn, BDL-E5+ and BDL-E5+ populations of cells were more demarcated; SC-ASCs showed higher percentage of cells (~33%) staining positively for BDL-E5 and ~11% of cells negatively for BDL-E5 (FIG. 4C(i)). VS-ASCs showed a decreased proportion of cells staining positively (~19%) for BDL-E5 and an increased percentage (~24%) of negative cells, as shown in FIG. 4C(ii). FIG. 10A (iii) and (iv) represents the unstained ASCs. BDL-E5+ and BDL-E5− cells sorted using FACS were seeded onto MEF-coated plates. Quantification of the number of iPS colonies formed after plating clearly indicated that BDL-E5+ SC-ASCs gave rise to more colonies than the BDL-E5− population (FIG. 4C(iii) and (iv)). Significantly, at least some BDL-E5+ VS-ASCs gave rise to iPS colonies whereas BDL-E5− VS-ASCs did not (FIG. 4C (iii) and (iv)). Thus these results demonstrate that BDL-E5 staining helps identify the cell population amenable to reprogramming, and increases the chance of generating iPS colonies from difficult-to-reprogram cell types such as VS-ASCs.

To investigate the quality of the BDL-E5+ generated iPS cells, the iPS colonies were passaged for several generations. As shown in FIG. 10B(i), ASC-derived BDL-E5+ colonies remained well self-renewed and TRA-1-60 positive for subsequent passages. However, BDL-E5− cells generated an average of only one colony, stained negative with TRA-1-60, and failed to form colonies upon subsequent passages (FIGS. 10B(ii) and C).

Example 5: BDL-E5+ Cells have Increased Expression of Pluripotency and Epithelial Markers The process of cellular reprogramming from somatic to iPS cells involves mesenchymal-epithelial transition (MET) and increased expression of pluripotency genes (Li et al., 2010; Samavarchi-Tehrani et al., 2010). DPSCs were reprogrammed and FACS was performed with BDL-E5 at 7 dpn. Expression of pluripotent, epithelial, and mesenchymal genes was measured using qPCR in BDL-E5+ (top 10%) and BDL-E5− (bottom 10%) cells. DiPS (dissociated into single cells) and DPSCs (non-reprogrammed) populations were also sorted by FACS and collected as positive and negative controls, respectively. As shown in FIG. 5A-D, BDL-E5+ cells exhibited increased expression of pluripotency genes, DNMT3B, GDF3, Nanog, LIN28 and DPPA2, and epithelial genes, Cdh1 and EpCAM1, compared with BDL-E5− cells. The increased expression of these genes in BDL-E5+ cells was comparable to that of DiPS cells, and decreased expression of these genes in BDL-E5− cells was comparable to that of DPSCs. qPCR was used to measure expression of mesenchymal genes, ZEB1, ZEB2, Snail1, Snail2, TGF-β1, FN1 and Activin A (FIGS. 5E-H). BDL-E5+ cells showed decreased expression of ZEB2, Snail2 and FN1 compared with BDL-E5− cells. BDL-E5− cells showed increased expression of mesenchymal genes comparable to DPSCs. Gene expression measurements using qPCR in reprogrammed ASCs sorted with BDL-E5 at 14 dpn showed increased LIN28 and Nanog expression in BDL-E5+ cells, while BDL-E5− cells showed significantly increased expression of TGF-β1 and slightly increased expression of Activin A, with a trend similar to AiPS versus ASCs (FIG. 11A).

To confirm that BDL-E5+-derived iPS cells are bona fide pluripotent cells, the inventors generated embyoid bodies and allowed the cells to spontaneously differentiate in vitro. The differentiated cells were then subjected to three-germ layer immunohistochemistry. As shown in FIG. 11B(i), the differentiated cells exhibited positive staining for all three germ layers including ectodermal TUJ1, mesodermal SMA and endodermal AFP. The qPCR analysis also indicated that the spontaneously differentiated cells derived from BDL-E5+ iPS cells showed increased gene expression of ectodermal GATA2, mesodermal SMA and endodermal AFP and SOX7 (FIG. 11B(ii)-(v)). Hence these results supported authenticity of the BDL-E5+-derived iPS cells.

Example 6: Bdl-E5 Detects Ips Cells Generated with Common Protocols or Three

Dimensional (3d) Culture Conditions, and May Localize to the Golgi Complex

In order to test whether BDL-E5 would be useful for identifying reprogramming and iPS cells in 3D culture suitable for large scale production, ASCs and DPSCs were reprogrammed and seeded on Geltrex-coated Cytodex 3 microcarriers prior to staining with BDL-E5 and TRA-1-60. As shown in FIG. 11C, BDL-E5 staining was clearly observed in reprogrammed cells in both cell lines, and pluripotency of the iPS cells formed on the microcarriers was confirmed using TRA-1-60 staining. The Cytodex 3 microcarriers themselves had no background BDL-E5 staining and the reprogrammed cells were readily distinguishable with intense fluorescence, at both 14 and 21 dpn.

To determine the subcellular organelle localization of BDL-E5 in reprogramming cells, 7 dpn DPSCs on MG were stained for BDL-E5 and organelle marker dyes for endoplasmic reticulum (ER), Golgi complex, lysosome, or mitochondria. Confocal images showed that BDL-E5 staining appeared to co-localize significantly with Golgi complex staining, and not with other organelle markers (FIG. 11D).

We also tested whether BDL-E5 worked for commonly used reprogramming methods and cell type. DPSCs were infected with retroviral vectors expressing four Yamanaka factors, and plated onto MEF. BDL-E5 similarly stained reprogramming cells as early as 7 days post-infection (dpi), when TRA-1-60 failed to detect any cells (FIG. 12A). In addition, BJ human fibroblasts were reprogrammed with lentiviral Yamanaka factors. BDL-E5 successfully stained reprogramming, but not non-reprogramming cells, and staining was stronger than that of TRA-1-60 (FIGS. 12B and C).

Figure 6:
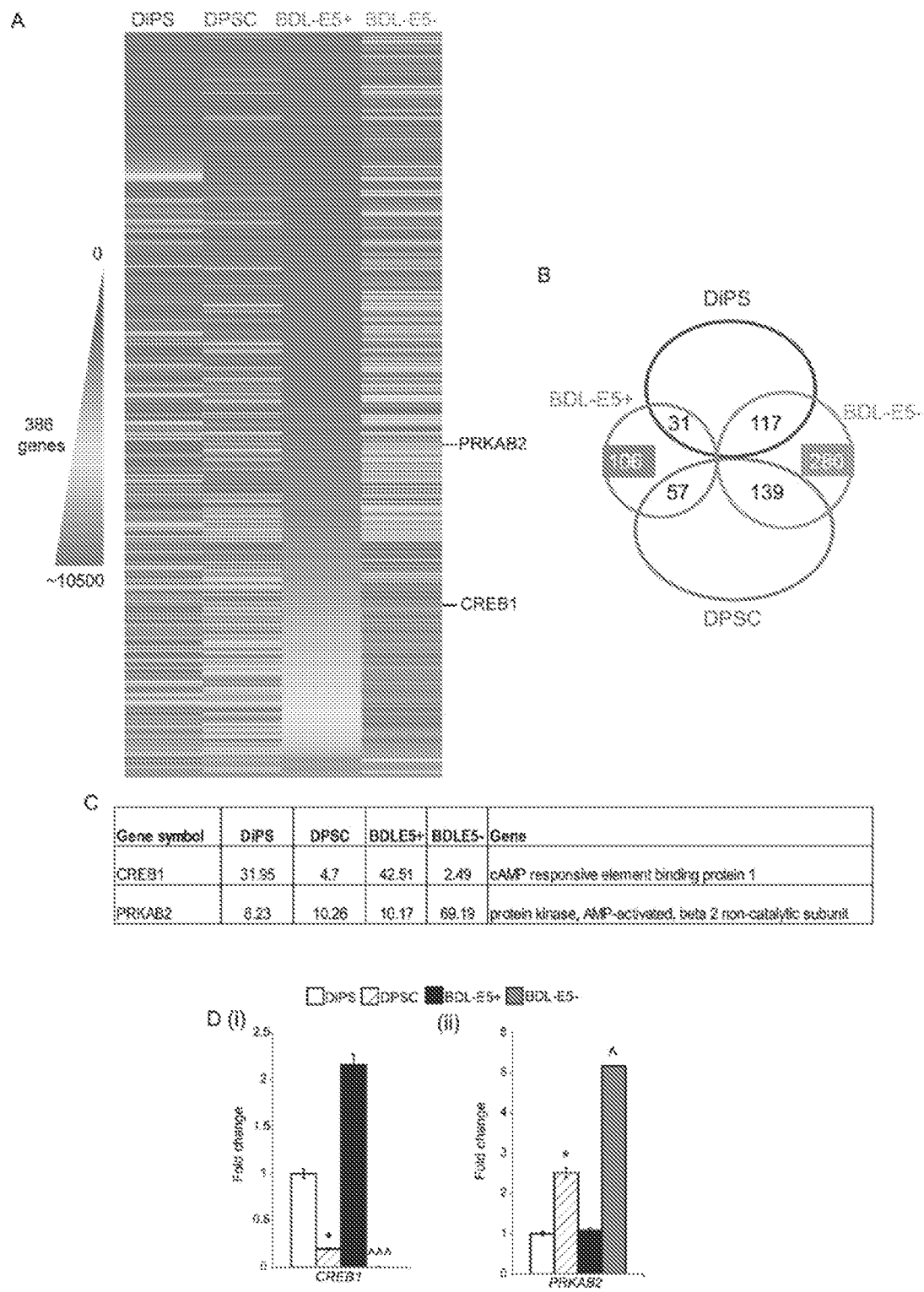
FIG. 6: (A) Heatmap showing 386 differentially expressed genes (between BDL-E5$^+$ and BDL-E5$^-$ cells) after RNA sequencing of four cell types (DiPS, DPSC, BDL-E5$^+$ and BDL-E5$^-$ cells) after FACS at 7 dpn of DPSC2 upon reprogramming (n=2). (B) Venn diagram showing the number of genes up-regulated in BDL-E5$^+$ and BDL-E5$^-$ cells, as obtained from RNA sequencing data. A total of 386 genes were differentially expressed significantly between the two cell types. (C) Table showing the relevant genes that were differentially expressed among DiPS, DPSC, BDL-E5$^+$, and BDL-E5$^-$ cells. (D) Graphs showing mRNA expression of CREB1 (i) and PRKAB2 (ii) obtained by qPCR from RNA isolated from DiPS, DPSC, BDL-E5$^+$, and BDL-E5$^-$ cells of DPSC2 obtained after FACS at 7 dpn (n=3). *p<0.05 denotes significance compared with DiPS; ^p<0.05 and ^^^p<0.001 denote significance compared with BDL-E5$^+$.

Example 7: RNA-Sequencing Analysis Reveals Early Reprogramming Markers in BDL-E5+ Cells To identify classes of novel genes that might be involved in early reprogramming stages defined by BDL-E5, RNA sequencing was performed on BDL-E5+ and BDL-E5− DPSCs sorted at 7 dpn, using DPSCs and DiPS cells as reference controls. Genes showing statistical significance ($p<0.05$) and >2 fold change were selected for analysis and, overall, 386 genes (shown in Table 2) were significantly differentially expressed (106 upregulated and 280 downregulated) in BDL-E5+ versus BDL-E5− sorted cells as shown in a heatmap and Venn diagram (FIGS. 6A and 6B). Further analysis of the 386 differentially expressed genes was carried out. Among the BDL-E5+ upregulated genes, 31 genes were expressed higher and 57 genes were expressed lower in DiPS cells compared with DPSCs. On the other hand, 117 genes were expressed higher and 139 genes were expressed lower in DiPS cells than DPSCs among the BDL-E5+ downregulated genes. Annotation using Ingenuity Pathway indicated that differentially regulated genes in BDL-E5+ versus BDL-E5− cells were associated with "embryonic development", "organismal development," and "tissue development" categories. Top canonical pathway and molecular cellular functions included "BMP signaling pathway," "FGF signaling," "cell-to-cell signaling and interaction," "cellular assembly and organization," and "cellular growth and proliferation" (FIG. 13A). Another analysis was performed using Metascape and demonstrated that the top enriched clusters between BDL-E5+ and BDL-E5− cells included "lamellipodium morphogenesis," "positive regulation of organelle organization," "regulation of transporter activity," "cell morphogenesis involved in neuron differentiation," and "embryo development" (FIG. 13B).

Among these, the inventors were particularly interested in CREB1 and PRKAB2 genes due to their potential involvement in the metabolic reprogramming process (FIGS. 6A and 6C). Expression of CREB1 was significantly upregulated in BDL-E5+ cells compared with BDL-E5− cells. CREB1 was also upregulated in DiPS cells. PRKAB2 was downregulated in both DiPS and BDL-E5+ cells. Gene expression was further confirmed by qPCR as shown in FIG. 6D. Based on these results, the inventors hypothesized that the pathway regulated by CREB1 may be involved in the early reprogramming process of cells that are marked by BDL-E5.

TABLE 2

List of the 386 genes differentially expressed in DiPS, DPSC, BDL-E5+, BDL-E5−

| Gene ID | Gene Symbol | DiPS | DPSC | BDL-E5+ | BDL-E5− | p value |
|---|---|---|---|---|---|---|
| ENSG00000029153.10 | ARNTL2 | 0.00 | 0.04 | 0.37 | 4.82 | 0.0188 |
| ENSG00000030304.8 | MUSK | 0.00 | 0.54 | 0.03 | 9.01 | 0.0089 |
| ENSG00000059378.8 | PARP12 | 0.00 | 19.17 | 9.55 | 86.06 | 0.0148 |
| ENSG00000068724.11 | TTC7A | 0.00 | 15.83 | 1.33 | 40.91 | 0.04115 |
| ENSG00000069869.11 | NEDD4 | 0.00 | 5.41 | 5.13 | 42.48 | 0.00865 |
| ENSG00000076258.5 | FMO4 | 0.00 | 9.28 | 0.00 | 1.25 | 0.00815 |
| ENSG00000090975.8 | PITPNM2 | 0.00 | 8.28 | 0.19 | 6.26 | 0.02695 |
| ENSG00000102078.11 | SLC25A14 | 0.00 | 54.00 | 1.34 | 146.61 | 0.001 |
| ENSG00000109667.7 | SLC2A9 | 0.00 | 0.00 | 1.26 | 0.00 | 5.00E−05 |
| ENSG00000117152.9 | RGS4 | 0.00 | 0.00 | 0.45 | 0.00 | 0.0056 |
| ENSG00000119725.13 | ZNF410 | 0.00 | 0.26 | 30.07 | 0.61 | 0.0031 |
| ENSG00000123243.10 | ITIH5 | 0.00 | 1.29 | 0.00 | 0.64 | 0.00055 |
| ENSG00000130382.7 | MLLT1 | 0.00 | 16.41 | 0.00 | 104.61 | 5.00E−05 |
| ENSG00000134007.3 | ADAM20 | 0.00 | 0.00 | 5.27 | 0.00 | 0.02535 |
| ENSG00000134539.12 | KLRD1 | 0.00 | 0.00 | 0.54 | 0.00 | 0.0143 |
| ENSG00000135362.9 | PRR5L | 0.00 | 5.56 | 0.80 | 21.84 | 0.00695 |
| ENSG00000138772.8 | ANXA3 | 0.00 | 0.00 | 3.12 | 128.24 | 0.0193 |
| ENSG00000141255.8 | SPATA22 | 0.00 | 0.00 | 0.00 | 0.69 | 0.0098 |
| ENSG00000143127.8 | ITGA10 | 0.00 | 2.80 | 0.58 | 0.00 | 0.01655 |
| ENSG00000148444.11 | COMMD3 | 0.00 | 63.25 | 35.07 | 273.40 | 0.03705 |
| ENSG00000152128.13 | TMEM163 | 0.00 | 0.00 | 0.00 | 68.59 | 5.00E−05 |
| ENSG00000154678.12 | PDE1C | 0.00 | 6.75 | 35.24 | 6.84 | 0.0365 |

TABLE 2-continued

List of the 386 genes differentially expressed in DiPS, DPSC, BDL-E5+, BDL-E5−

| Gene ID | Gene Symbol | DiPS | DPSC | BDL-E5+ | BDL-E5− | p value |
|---|---|---|---|---|---|---|
| ENSG00000158806.9 | NPM2 | 0.00 | 0.00 | 0.00 | 32.06 | 6.00E−04 |
| ENSG00000159314.7 | ARHGAP27 | 0.00 | 0.00 | 0.00 | 2.70 | 0.001 |
| ENSG00000161681.11 | SHANK1 | 0.00 | 0.00 | 0.00 | 0.55 | 0.00055 |
| ENSG00000164463.8 | CREBRF | 0.00 | 7.45 | 19.68 | 0.95 | 0.0135 |
| ENSG00000167136.6 | ENDOG | 0.00 | 3.97 | 2.83 | 0.00 | 0.03695 |
| ENSG00000167925.11 | GHDC | 0.00 | 3.88 | 0.03 | 50.77 | 3.00E−04 |
| ENSG00000168405.10 | CMAHP | 0.00 | 0.01 | 0.00 | 211.45 | 5.00E−05 |
| ENSG00000172733.10 | PURG | 0.00 | 0.19 | 0.00 | 4.09 | 0.04485 |
| ENSG00000173083.10 | HPSE | 0.00 | 0.00 | 0.43 | 30.85 | 0.048 |
| ENSG00000178685.9 | PARP10 | 0.00 | 2.15 | 0.97 | 214.51 | 0.03005 |
| ENSG00000183644.9 | C11orf88 | 0.00 | 2.26 | 0.67 | 0.00 | 0.01075 |
| ENSG00000184588.13 | PDE4B | 0.00 | 37.02 | 10.35 | 158.90 | 0.0108 |
| ENSG00000186998.11 | EMID1 | 0.00 | 0.00 | 0.00 | 0.40 | 0.0085 |
| ENSG00000196843.11 | ARID5A | 0.00 | 46.00 | 4.66 | 131.21 | 0.0251 |
| ENSG00000197182.8 | FLJ27365 | 0.00 | 3.53 | 0.49 | 23.02 | 0.036 |
| ENSG00000197584.7 | KCNMB2 | 0.00 | 0.00 | 0.00 | 0.59 | 0.02015 |
| ENSG00000198520.6 | C1orf228 | 0.00 | 0.00 | 0.00 | 79.96 | 0.04935 |
| ENSG00000205746.5 | RP11-1212A22.1 | 0.00 | 0.00 | 0.00 | 2.11 | 0.0332 |
| ENSG00000206127.6 | GOLGA8O | 0.00 | 0.92 | 1.75 | 0.00 | 0.04085 |
| ENSG00000215527.3 | AP005482.1 | 0.00 | 0.00 | 0.00 | 333.91 | 0.0039 |
| ENSG00000218996.1 | RP1-99E18.2 | 0.00 | 0.00 | 0.00 | 4.86 | 0.04195 |
| ENSG00000224080.1 | UBE2FP1 | 0.00 | 0.58 | 0.00 | 1.16 | 0.017 |
| ENSG00000224623.1 | RP11-247I13.8 | 0.00 | 0.00 | 2.28 | 0.00 | 0.02075 |
| ENSG00000225383.2 | SFTA1P | 0.00 | 0.00 | 0.00 | 11.76 | 0.0279 |
| ENSG00000225920.2 | RIMKLBP2 | 0.00 | 0.00 | 2.14 | 0.00 | 0.01615 |
| ENSG00000227953.2 | RP11-439E19.3 | 0.00 | 3.29 | 1.70 | 0.00 | 0.0181 |
| ENSG00000229052.2 | RP11-386123.1 | 0.00 | 0.66 | 0.91 | 0.00 | 0.02955 |
| ENSG00000229124.2 | VIM-AS1 | 0.00 | 0.02 | 0.53 | 0.00 | 0.01325 |
| ENSG00000229325.1 | ACAP2-IT1 | 0.00 | 0.00 | 14.51 | 0.00 | 0.03095 |
| ENSG00000229692.3 | SOS1-IT1 | 0.00 | 0.00 | 0.00 | 10.49 | 0.0421 |
| ENSG00000229808.1 | RP11-456P18.2 | 0.00 | 0.00 | 0.91 | 0.00 | 0.0258 |
| ENSG00000230001.1 | RP11-70J12.1 | 0.00 | 2.82 | 12.54 | 0.00 | 0.03395 |
| ENSG00000232116.2 | RP11-187C18.2 | 0.00 | 15.03 | 0.00 | 11.70 | 0.04865 |
| ENSG00000234636.1 | MED14-AS1 | 0.00 | 0.00 | 0.00 | 1.40 | 0.0281 |
| ENSG00000237654.1 | AP003025.2 | 0.00 | 1.14 | 0.00 | 22.22 | 0.04965 |
| ENSG00000237803.1 | LINC00211 | 0.00 | 0.00 | 0.00 | 0.29 | 0.03995 |
| ENSG00000238113.2 | RP11-262H14.1 | 0.00 | 0.28 | 0.00 | 3.42 | 0.0337 |
| ENSG00000240695.1 | RP11-102M11.1 | 0.00 | 20.15 | 0.00 | 1.77 | 0.03325 |
| ENSG00000241295.1 | ZBTB20-AS2 | 0.00 | 12.76 | 23.50 | 0.00 | 0.0494 |
| ENSG00000242154.1 | RP4-778K6.3 | 0.00 | 0.00 | 12.86 | 0.00 | 0.045 |
| ENSG00000243251.4 | PGBD3 | 0.00 | 9.15 | 13.42 | 0.00 | 0.0263 |
| ENSG00000243305.1 | RP11-362A9.3 | 0.00 | 1.72 | 0.00 | 4.01 | 0.01435 |
| ENSG00000248664.1 | CTC-498J12.3 | 0.00 | 0.00 | 0.00 | 0.40 | 0.0166 |
| ENSG00000249593.2 | CTB-46B19.2 | 0.00 | 0.00 | 0.32 | 0.00 | 0.0388 |
| ENSG00000251381.2 | LINC00958 | 0.00 | 0.00 | 0.28 | 0.00 | 0.0079 |
| ENSG00000255139.1 | AP000442.1 | 0.00 | 0.00 | 0.00 | 178.60 | 0.0076 |
| ENSG00000256025.1 | CACNA1C-AS4 | 0.00 | 4.99 | 0.00 | 41.02 | 0.0065 |
| ENSG00000256390.1 | AC092143.1 | 0.00 | 0.00 | 0.41 | 0.00 | 0.01655 |
| ENSG00000256469.1 | RP11-856F16.2 | 0.00 | 1.63 | 0.00 | 6.09 | 0.0419 |
| ENSG00000258978.1 | HIF1AP1 | 0.00 | 0.00 | 0.00 | 124.37 | 0.01085 |
| ENSG00000259948.2 | RP11-326A19.5 | 0.00 | 0.00 | 0.68 | 0.00 | 0.02955 |
| ENSG00000260946.1 | RP11-407G23.3 | 0.00 | 27.94 | 0.00 | 74.33 | 0.0244 |
| ENSG00000261355.1 | RP11-698N11.4 | 0.00 | 0.17 | 2.90 | 0.00 | 5.00E−05 |
| ENSG00000261777.1 | RP11-529K1.2 | 0.00 | 0.00 | 0.70 | 0.00 | 0.0238 |
| ENSG00000262211.1 | CTD-2031P19.5 | 0.00 | 0.00 | 4.09 | 0.00 | 0.0189 |
| ENSG00000267395.1 | AC074212.6 | 0.00 | 7.25 | 2.62 | 0.00 | 0.02365 |
| ENSG00000267515.1 | RP11-861E21.3 | 0.00 | 0.00 | 27.81 | 0.00 | 0.0282 |
| ENSG00000267811.1 | RP11-727F15.11 | 0.00 | 1.03 | 6.34 | 0.00 | 0.011 |
| ENSG00000269997.1 | RP11-214K3.21 | 0.00 | 0.00 | 0.00 | 211.50 | 0.0488 |
| ENSG00000272533.1 | SNORA28 | 0.00 | 0.00 | 519.97 | 0.00 | 0.0036 |
| ENSG00000272991.1 | AF129408.17 | 0.00 | 31.84 | 31.93 | 0.00 | 0.0139 |
| ENSG00000273297.1 | RP11-38M8.1 | 0.00 | 0.76 | 7.39 | 0.00 | 0.0271 |
| ENSG00000273384.1 | RP5-1098D14.1 | 0.00 | 0.00 | 0.00 | 138.30 | 0.01545 |
| ENSG00000271741.1 | ZMYM6 | 0.00 | 0.03 | 1.77 | 0.00 | 0.04815 |
| ENSG00000250802.2 | ZBED3-AS1 | 0.00 | 0.00 | 1.41 | 0.00 | 0.0187 |
| ENSG00000172716.12 | SLFN11 | 0.00 | 4.19 | 23.14 | 0.40 | 0.0229 |
| ENSG00000196724.8 | ZNF418 | 0.00 | 0.98 | 0.00 | 0.77 | 0.01825 |
| ENSG00000107738.15 | C10orf154 | 0.00 | 49.53 | 55.13 | 11.04 | 0.0382 |
| ENSG00000155066.11 | PROM2 | 0.00 | 0.00 | 0.00 | 0.42 | 0.00015 |
| ENSG00000144810.11 | COL8A1 | 0.01 | 24.25 | 27.76 | 110.32 | 0.03055 |
| ENSG00000163412.8 | EIF4E3 | 0.01 | 1.09 | 1.39 | 0.07 | 0.01515 |
| ENSG00000113296.10 | THBS4 | 0.01 | 0.00 | 0.00 | 12.35 | 0.0023 |
| ENSG00000123552.13 | USP45 | 0.01 | 2.64 | 17.58 | 1.72 | 0.01925 |
| ENSG00000137809.12 | ITGA11 | 0.01 | 54.05 | 43.73 | 178.38 | 0.03325 |
| ENSG00000175787.12 | ZNF169 | 0.02 | 0.01 | 0.00 | 2.61 | 0.0192 |
| ENSG00000105605.3 | CACNG7 | 0.02 | 0.05 | 0.00 | 0.43 | 0.0316 |

TABLE 2-continued

List of the 386 genes differentially expressed in DiPS, DPSC, BDL-E5+, BDL-E5−

| Gene ID | Gene Symbol | DiPS | DPSC | BDL-E5+ | BDL-E5− | p value |
|---|---|---|---|---|---|---|
| ENSG00000198690.5 | FAN1 | 0.02 | 0.49 | 2.89 | 0.25 | 0.03 |
| ENSG00000142794.14 | NBPF3 | 0.02 | 4.98 | 0.05 | 0.37 | 0.01015 |
| ENSG00000006283.13 | CACNA1G | 0.03 | 0.04 | 0.00 | 0.58 | 0.0013 |
| ENSG00000132256.14 | TRIM5 | 0.03 | 37.19 | 1.75 | 38.68 | 0.0078 |
| ENSG00000213073.4 | RP11-288H12.3 | 0.03 | 0.00 | 0.00 | 36.39 | 0.00625 |
| ENSG00000214176.5 | PLEKHM1P | 0.04 | 5.89 | 0.01 | 4.55 | 0.0222 |
| ENSG00000135297.11 | MTO1 | 0.04 | 0.16 | 0.87 | 34.48 | 0.0013 |
| ENSG00000259571.1 | BLID | 0.04 | 104.78 | 2.91 | 0.00 | 0.03145 |
| ENSG00000110756.13 | HPS5 | 0.05 | 0.26 | 33.82 | 6.38 | 0.04325 |
| ENSG00000239713.3 | APOBEC3G | 0.05 | 0.13 | 3.51 | 0.04 | 0.03025 |
| ENSG00000159403.11 | C1R | 0.06 | 1182.24 | 205.29 | 848.86 | 0.0167 |
| ENSG00000112769.14 | LAMA4 | 0.07 | 121.77 | 38.18 | 340.15 | 0.00175 |
| ENSG00000142330.15 | CAPN10 | 0.07 | 30.00 | 0.78 | 165.69 | 5.00E−05 |
| ENSG00000256594.3 | RP11-705C15.2 | 0.07 | 0.66 | 0.00 | 4.84 | 0.0411 |
| ENSG00000138639.13 | ARHGAP24 | 0.07 | 0.00 | 85.90 | 0.34 | 0.00665 |
| ENSG00000181938.9 | GINS3 | 0.08 | 0.07 | 0.00 | 0.64 | 0.0057 |
| ENSG00000219470.1 | RP3-337H4.6 | 0.08 | 0.17 | 0.83 | 0.00 | 0.0459 |
| ENSG00000272899.1 | RP11-309L24.9 | 0.08 | 0.15 | 9.22 | 0.00 | 0.00605 |
| ENSG00000134802.13 | SLC43A3 | 0.09 | 0.14 | 1.48 | 0.06 | 0.0071 |
| ENSG00000204991.6 | SPIRE2 | 0.09 | 3.73 | 0.00 | 0.37 | 0.00115 |
| ENSG00000261552.1 | RP11-2641317.5 | 0.09 | 27.02 | 0.00 | 64.44 | 0.0378 |
| ENSG00000235865.2 | GSN-ASI | 0.10 | 5.55 | 0.08 | 9.57 | 0.04845 |
| ENSG00000183023.14 | SLC8A1 | 0.11 | 19.12 | 3.02 | 65.61 | 0.0257 |
| ENSG00000146373.12 | RNF217 | 0.11 | 8.19 | 1.31 | 6.25 | 0.02805 |
| ENSG00000121964.10 | GTDC1 | 0.11 | 4.26 | 2.52 | 76.83 | 0.0119 |
| ENSG00000203836.7 | NBPF24 | 0.13 | 0.04 | 0.00 | 2.79 | 0.02085 |
| ENSG00000175984.10 | DENND2C | 0.15 | 0.01 | 0.48 | 9.77 | 0.0095 |
| ENSG00000119681.7 | LTBP2 | 0.16 | 8.83 | 5.10 | 44.40 | 0.01055 |
| ENSG00000269242.1 | CTD-2192J16.22 | 0.18 | 7.03 | 35.91 | 0.00 | 0.02355 |
| ENSG00000183655.11 | KLHL25 | 0.18 | 0.14 | 0.00 | 1.15 | 0.0423 |
| ENSG00000196159.7 | FAT4 | 0.18 | 8.16 | 4.10 | 16.21 | 0.03155 |
| ENSG00000167972.9 | ABCA3 | 0.20 | 0.00 | 0.00 | 2.58 | 0.0303 |
| ENSG00000140471.12 | LINS | 0.21 | 78.54 | 0.50 | 82.48 | 0.01345 |
| ENSG00000235034.2 | C19orf81 | 0.22 | 2.90 | 0.00 | 0.74 | 0.0489 |
| ENSG00000138134.7 | STAMBPL1 | 0.22 | 0.01 | 0.00 | 7.50 | 0.03875 |
| ENSG00000151883.12 | PARP8 | 0.23 | 0.00 | 0.01 | 0.26 | 0.00025 |
| ENSG00000183405.5 | RPS7P1 | 0.23 | 0.21 | 0.54 | 0.00 | 0.03545 |
| ENSG00000213707.2 | HMGB1P10 | 0.23 | 0.48 | 0.00 | 5.47 | 0.01645 |
| ENSG00000204084.8 | INPP5B | 0.23 | 0.54 | 0.65 | 17.81 | 0.03345 |
| ENSG00000160469.12 | BRSK1 | 0.24 | 0.00 | 0.00 | 1.25 | 0.0152 |
| ENSG00000072518.16 | MARK2 | 0.26 | 0.18 | 1.14 | 24.73 | 0.02035 |
| ENSG00000146263.7 | MMS22L | 0.27 | 0.25 | 0.00 | 5.45 | 5.00E−05 |
| ENSG00000021645.13 | NRXN3 | 0.30 | 0.02 | 8.17 | 0.00 | 5.00E−05 |
| ENSG00000185278.10 | ZBTB37 | 0.30 | 2.64 | 0.01 | 0.59 | 0.02725 |
| ENSG00000139926.11 | FRMD6 | 0.35 | 26.83 | 55.29 | 458.21 | 0.00925 |
| ENSG00000223953.3 | C1QTNF5 | 0.36 | 204.94 | 201.46 | 1600.38 | 0.00135 |
| ENSG00000166311.5 | SMPD1 | 0.38 | 94.15 | 112.34 | 585.07 | 0.02725 |
| ENSG00000129657.10 | SEC14L1 | 0.40 | 19.75 | 73.50 | 19.64 | 0.03895 |
| ENSG00000105483.12 | CARD8 | 0.45 | 22.43 | 0.66 | 14.91 | 0.02 |
| ENSG00000161958.6 | FGF11 | 0.51 | 1.71 | 0.33 | 18.23 | 0.0171 |
| ENSG00000167615.12 | LENG8 | 0.54 | 24.86 | 1.75 | 177.96 | 0.01025 |
| ENSG00000160828.13 | STAG3L2 | 0.58 | 9.10 | 0.27 | 5.50 | 0.0252 |
| ENSG00000260793.2 | RPS-882C2.2 | 0.63 | 2.04 | 3.70 | 0.00 | 0.01455 |
| ENSG00000106648.9 | GALNTL5 | 0.64 | 0.06 | 0.00 | 0.67 | 0.0041 |
| ENSG00000157869.10 | RAB28 | 0.64 | 1.06 | 14.07 | 73.16 | 0.0405 |
| ENSG00000158773.10 | USF1 | 0.69 | 13.14 | 13.84 | 0.00 | 0.022 |
| ENSG00000229809.4 | ZNF688 | 0.72 | 5.79 | 0.76 | 40.82 | 0.013 |
| ENSG00000232931.1 | LINC00342 | 0.73 | 6.33 | 8.56 | 64.96 | 0.02945 |
| ENSG00000141576.10 | RNF157 | 0.84 | 0.00 | 0.51 | 0.01 | 0.04825 |
| ENSG00000255248.2 | RP11-166D19.1 | 0.86 | 138.45 | 33.59 | 207.41 | 0.0227 |
| ENSG00000118762.3 | PKD2 | 0.86 | 28.76 | 39.41 | 8.30 | 0.0392 |
| ENSG00000147457.9 | CHMP7 | 0.88 | 11.38 | 37.02 | 4.23 | 0.0461 |
| ENSG00000106608.12 | URGCP | 0.89 | 1.17 | 51.04 | 0.35 | 0.0022 |
| EN8G00000162928.8 | PEX13 | 0.95 | 4.92 | 4.36 | 146.84 | 0.0077 |
| ENSG00000090674.11 | MCOLN1 | 1.05 | 60.52 | 0.76 | 19.86 | 0.0332 |
| ENSG00000073711.6 | PPP2R3A | 1.11 | 6.57 | 4.59 | 29.75 | 0.04325 |
| ENSG00000229153.1 | EPHA1-AS1 | 1.12 | 0.24 | 5.52 | 0.00 | 0.00925 |
| ENSG00000232586.1 | RP11-46A10.4 | 1.16 | 0.06 | 0.00 | 0.58 | 0.01455 |
| ENSG00000122481.12 | RWDD3 | 1.21 | 63.16 | 39.82 | 225.43 | 0.0445 |
| ENSG00000136720.6 | HS6ST1 | 1.21 | 60.37 | 23.29 | 123.76 | 0.0454 |
| ENSG00000188130.9 | MAPK12 | 1.29 | 51.40 | 65.20 | 1.23 | 0.0202 |
| ENSG00000133250.9 | ZNF414 | 1.31 | 0.32 | 0.00 | 24.34 | 0.0045 |
| ENSG00000160352.11 | ZNF714 | 1.32 | 0.24 | 0.00 | 0.97 | 0.0136 |
| ENSG00000172725.9 | CORO1B | 1.34 | 1.67 | 19.94 | 1.33 | 0.0099 |
| ENSG00000236526.1 | RP4-742J24.2 | 1.35 | 12.53 | 1.22 | 0.00 | 0.0318 |
| ENSG00000150712.6 | MTMR12 | 1.35 | 5.44 | 6.96 | 0.39 | 0.02425 |

TABLE 2-continued

List of the 386 genes differentially expressed in DiPS, DPSC, BDL-E5+, BDL-E5−

| Gene ID | Gene Symbol | DiPS | DPSC | BDL-E5+ | BDL-E5− | p value |
|---|---|---|---|---|---|---|
| ENSG00000074527.7 | NTN4 | 1.36 | 22.30 | 203.79 | 47.63 | 0.03745 |
| ENSG00000197016.7 | ZNF470 | 1.52 | 0.08 | 0.13 | 4.08 | 0.0473 |
| ENSG00000164338.5 | UTP15 | 1.56 | 2.37 | 1.61 | 57.46 | 0.0041 |
| ENSG00000206560.6 | ANKRD28 | 1.66 | 65.12 | 5.10 | 79.01 | 0.006 |
| ENSG00000075539.9 | FRYL | 1.85 | 170.14 | 5.05 | 44.67 | 0.02035 |
| ENSG00000268093.1 | AC022154.7 | 1.88 | 1.09 | 0.00 | 0.50 | 0.0292 |
| ENSG00000125962.10 | ARMCX5 | 1.92 | 0.11 | 1.52 | 59.32 | 0.03555 |
| ENSG00000129911.4 | KLF16 | 1.93 | 3.55 | 0.99 | 32.26 | 0.04305 |
| ENSG00000164877.14 | MICALL2 | 1.96 | 62.11 | 32.67 | 229.73 | 0.0311 |
| ENSG00000257647.1 | RP11-701H24.3 | 2.00 | 0.94 | 0.00 | 10.99 | 0.02645 |
| ENSG00000115966.12 | ATF2 | 2.09 | 7.12 | 41.34 | 5.69 | 0.0267 |
| ENSG00000160216.14 | AGPAT3 | 2.12 | 4.83 | 5.54 | 47.29 | 0.02025 |
| ENSG00000256525.2 | POLG2 | 2.16 | 10.31 | 0.43 | 15.15 | 0.0276 |
| ENSG00000149929.11 | HIRIP3 | 2.26 | 4.78 | 25.38 | 0.03 | 0.0474 |
| ENSG00000174684.6 | B3GNT1 | 2.30 | 39.47 | 17.05 | 105.05 | 0.0474 |
| ENSG00000105559.7 | PLEKHA4 | 2.40 | 28.99 | 8.83 | 83.57 | 0.02915 |
| ENSG00000187609.11 | EXD3 | 2.49 | 30.13 | 4.28 | 118.89 | 0.00825 |
| ENSG00000185046.14 | ANKS1B | 2.49 | 0.51 | 0.44 | 0.00 | 0.0165 |
| ENSG00000184381.14 | PLA2G6 | 2.51 | 0.19 | 0.00 | 1.43 | 0.00255 |
| ENSG00000136436.10 | CALCOCO2 | 2.66 | 22.13 | 46.79 | 333.30 | 0.0178 |
| ENSG00000213918.6 | DNASE1 | 2.66 | 8.69 | 16.15 | 1.03 | 0.04625 |
| ENSG00000161395.8 | PGAP3 | 2.77 | 4.93 | 0.68 | 54.65 | 0.03815 |
| ENSG00000204196.4 | AC011737.2 | 2.78 | 2.52 | 0.75 | 99.18 | 0.02925 |
| ENSG00000103111.10 | MON1B | 2.83 | 22.08 | 44.23 | 1.76 | 0.0113 |
| ENSG00000269279.1 | AL136376.1 | 2.91 | 4.08 | 0.00 | 5.41 | 0.01205 |
| ENSG00000139579.8 | NABP2 | 2.94 | 6.26 | 0.77 | 47.39 | 0.03925 |
| ENSG00000154370.9 | TRIM11 | 3.17 | 9.59 | 0.73 | 30.51 | 0.0225 |
| ENSG00000104081.9 | BMF | 3.20 | 0.45 | 0.03 | 47.46 | 3.00E−04 |
| ENSG00000145012.8 | LPP | 3.56 | 10.43 | 10.98 | 120.27 | 0.0096 |
| ENSG00000113716.8 | HMGXB3 | 3.67 | 1.67 | 0.70 | 31.38 | 0.02915 |
| ENSG00000241258.2 | CRCP | 3.73 | 38.44 | 21.51 | 2.48 | 0.0467 |
| ENSG00000198380.8 | GFPT1 | 3.79 | 4.53 | 9.62 | 93.28 | 0.0223 |
| ENSG00000166912.12 | MTMR10 | 3.90 | 8.82 | 5.29 | 33.69 | 0.0355 |
| ENSG00000267542.1 | RP11-697E22.1 | 3.95 | 11.63 | 12.97 | 0.00 | 0.0377 |
| ENSG00000253251.2 | CTC-534A2.2 | 4.15 | 5.41 | 0.00 | 3.86 | 0.04345 |
| ENSG00000138035.10 | PNPT1 | 4.37 | 0.72 | 0.87 | 19.99 | 0.0243 |
| ENSG00000105321.8 | CCDC9 | 4.37 | 0.02 | 1.11 | 0.00 | 0.007 |
| ENSG00000103260.4 | METRN | 4.43 | 48.99 | 2.57 | 133.57 | 0.008 |
| ENSG00000269388.1 | AC018755.16 | 4.48 | 0.00 | 0.00 | 1.31 | 0.0316 |
| ENSG00000198954.4 | KIAA1279 | 4.61 | 19.18 | 8.65 | 70.08 | 0.0416 |
| ENSG00000075420.8 | FNDC3B | 4.80 | 20.14 | 40.04 | 230.59 | 0.0327 |
| ENSG00000157353.12 | FUK | 4.81 | 5.11 | 0.47 | 34.19 | 0.0492 |
| ENSG00000256904.1 | A2ML1-AS2 | 4.91 | 0.00 | 0.00 | 1.29 | 0.01695 |
| ENSG00000177873.8 | ZNF619 | 5.02 | 0.02 | 0.00 | 1.40 | 0.0155 |
| ENSG00000125846.11 | ZNF133 | 5.12 | 2.29 | 0.71 | 34.67 | 0.00535 |
| ENSG00000118518.11 | RNF146 | 5.16 | 7.44 | 10.78 | 121.79 | 0.01285 |
| ENSG00000160055.15 | TMEM234 | 5.22 | 0.97 | 6.59 | 0.19 | 0.04965 |
| ENSG00000132004.8 | FBXW9 | 5.31 | 21.06 | 2.55 | 67.37 | 0.03545 |
| ENSG00000131724.6 | IL13RA1 | 5.32 | 9.09 | 21.38 | 4.19 | 0.0234 |
| ENSG00000196810.4 | CTBP1-AS2 | 5.33 | 14.28 | 0.12 | 82.99 | 0.00365 |
| ENSG00000186862.13 | PDZD7 | 5.49 | 1.83 | 0.15 | 4.38 | 0.04035 |
| ENSG00000243335.4 | KCTD7 | 5.51 | 0.13 | 0.36 | 13.44 | 0.0414 |
| ENSG00000078246.11 | TULP3 | 5.68 | 4.64 | 5.79 | 194.84 | 0.02755 |
| ENSG00000198055.6 | GRK6 | 5.69 | 1.72 | 0.07 | 5.69 | 0.03345 |
| ENSG00000149930.13 | TAOK2 | 6.12 | 3.42 | 0.55 | 14.52 | 0.0332 |
| ENSG00000140367.7 | UBE2Q2 | 6.24 | 16.84 | 3.26 | 21.11 | 0.04405 |
| ENSG00000175866.11 | BAIAP2 | 6.27 | 3.32 | 57.96 | 4.18 | 0.00785 |
| ENSG00000167257.6 | RNF214 | 6.44 | 4.30 | 1.46 | 15.98 | 0.02625 |
| ENSG00000175567.4 | UCP2 | 6.48 | 0.00 | 0.00 | 1.83 | 0.02095 |
| ENSG00000033178.8 | UBA6 | 6.52 | 24.99 | 7.56 | 61.16 | 0.01225 |
| ENSG00000157456.3 | CCNB2 | 6.99 | 0.00 | 0.00 | 1.33 | 0.04925 |
| ENSG00000145860.7 | RNF145 | 7.09 | 17.06 | 7.28 | 92.04 | 0.03475 |
| ENSG00000146243.9 | IRAK1BP1 | 7.16 | 1.61 | 6.18 | 0.07 | 0.03085 |
| ENSG00000130669.13 | PAK4 | 7.20 | 2.21 | 13.55 | 0.93 | 0.02925 |
| ENSG00000180881.15 | CAPS2 | 7.38 | 0.45 | 0.10 | 18.70 | 0.00205 |
| ENSG00000079739.11 | PGM1 | 7.57 | 15.02 | 30.84 | 179.18 | 0.03445 |
| ENSG00000108830.7 | RND2 | 7.63 | 0.00 | 0.00 | 0.58 | 0.04305 |
| ENSG00000168528.7 | SERINC2 | 8.13 | 12.66 | 23.44 | 193.70 | 0.03645 |
| ENSG00000131196.13 | NFATC1 | 8.17 | 2.59 | 0.93 | 47.76 | 8.00E−04 |
| ENSG00000131791.6 | PRKAB2 | 8.24 | 10.26 | 10.18 | 69.19 | 0.0279 |
| ENSG00000176105.9 | YES1 | 8.75 | 7.29 | 5.68 | 33.89 | 0.0442 |
| ENSG00000100479.8 | POLE2 | 8.90 | 5.62 | 11.80 | 0.00 | 0.0459 |
| ENSG00000124782.15 | RREB1 | 8.96 | 25.10 | 1.97 | 89.52 | 0.02475 |
| ENSG00000151746.9 | BICD1 | 9.06 | 1.76 | 0.61 | 11.99 | 0.02745 |
| ENSG00000110422.7 | HIPK3 | 9.20 | 10.84 | 5.34 | 24.44 | 0.049 |
| ENSG00000168758.6 | SEMA4C | 9.32 | 0.83 | 0.40 | 0.00 | 0.01885 |

TABLE 2-continued

List of the 386 genes differentially expressed in DiPS, DPSC, BDL-E5+, BDL-E5−

| Gene ID | Gene Symbol | DiPS | DPSC | BDL-E5+ | BDL-E5− | p value |
|---|---|---|---|---|---|---|
| ENSG00000107779.7 | BMPR1A | 9.82 | 2.90 | 1.69 | 13.06 | 0.0123 |
| ENSG00000117713.13 | ARID1A | 9.88 | 5.75 | 2.74 | 27.83 | 0.0214 |
| ENSG00000151348.9 | EXT2 | 9.93 | 57.52 | 38.28 | 9.35 | 0.03815 |
| ENSG00000001631.10 | KRIT1 | 10.04 | 7.02 | 5.06 | 134.21 | 0.0125 |
| ENSG00000177885.9 | GRB2 | 10.04 | 88.12 | 31.28 | 338.39 | 0.03615 |
| ENSG00000131323.10 | TRAF3 | 10.26 | 3.50 | 3.35 | 0.07 | 0.028 |
| ENSG00000110075.10 | PPP6R3 | 10.72 | 23.86 | 16.20 | 87.31 | 0.024 |
| ENSG00000163935.9 | SFMBT1 | 11.68 | 2.11 | 0.21 | 89.49 | 0.01245 |
| ENSG00000006468.9 | ETV1 | 11.78 | 0.00 | 0.00 | 8.05 | 5.00E−05 |
| ENSG00000184347.10 | SLIT3 | 11.81 | 12.31 | 16.97 | 171.65 | 0.04765 |
| ENSG00000119689.10 | DLST | 11.92 | 1.88 | 30.21 | 0.07 | 0.00345 |
| ENSG00000181027.6 | FKRP | 12.13 | 4.73 | 1.48 | 106.76 | 0.04255 |
| ENSG00000113312.6 | TTC1 | 12.40 | 126.88 | 354.60 | 72.10 | 0.023 |
| ENSG00000177943.9 | MAMDC4 | 12.55 | 7.26 | 0.00 | 1.00 | 0.0257 |
| ENSG00000105127.4 | AKAP8 | 12.66 | 15.52 | 1.54 | 38.75 | 0.02535 |
| ENSG00000125459.10 | MSTO1 | 12.88 | 1.59 | 0.19 | 5.84 | 0.0181 |
| ENSG00000161202.13 | DVL3 | 12.95 | 18.30 | 2.19 | 51.52 | 0.01915 |
| ENSG00000121152.5 | NCAPH | 14.46 | 0.00 | 0.00 | 63.91 | 0.01595 |
| ENSG00000156970.8 | BUB1B | 14.58 | 0.00 | 0.06 | 2.81 | 0.047 |
| ENSG00000138190.12 | EXOC6 | 14.73 | 0.09 | 0.10 | 10.43 | 0.0127 |
| ENSG00000153250.13 | RBMS1 | 15.14 | 144.93 | 48.51 | 235.58 | 0.01575 |
| ENSG00000124155.12 | PIGT | 15.15 | 109.11 | 95.81 | 353.88 | 0.04185 |
| ENSG00000196526.6 | AFAP1 | 15.19 | 26.76 | 5.47 | 92.03 | 0.0186 |
| ENSG00000170310.10 | STX8 | 16.50 | 40.57 | 267.05 | 1088.17 | 0.0152 |
| ENSG00000145014.13 | TMEM44 | 18.58 | 28.86 | 14.34 | 0.73 | 0.0469 |
| ENSG00000088833.13 | NSFL1C | 18.81 | 16.25 | 87.23 | 9.00 | 0.042 |
| ENSG00000127580.11 | WDR24 | 19.13 | 6.16 | 0.35 | 36.69 | 0.04805 |
| ENSG00000196313.7 | POM121 | 19.33 | 2.06 | 0.11 | 39.20 | 0.0261 |
| ENSG00000103168.12 | TAF1C | 19.36 | 21.51 | 0.89 | 26.80 | 0.0283 |
| ENSG00000135506.11 | OS9 | 19.36 | 68.85 | 29.56 | 242.73 | 0.02475 |
| ENSG00000113734.13 | BNIP1 | 19.53 | 2.07 | 21.33 | 0.67 | 0.04895 |
| ENSG00000164543.5 | STK17A | 19.79 | 2.70 | 3.01 | 74.86 | 0.0051 |
| ENSG00000163006.7 | CCDC138 | 20.21 | 0.19 | 0.25 | 0.00 | 0.0038 |
| ENSG00000151657.7 | KIN | 20.34 | 66.80 | 11.57 | 124.07 | 0.0316 |
| ENSG00000126787.8 | DLGAP5 | 20.49 | 0.00 | 0.00 | 0.62 | 0.01385 |
| ENSG00000137942.12 | FNBP1L | 20.80 | 14.61 | 6.42 | 36.33 | 0.04555 |
| ENSG00000158195.6 | WASF2 | 20.87 | 99.75 | 79.55 | 679.26 | 0.03235 |
| ENSG00000243725.2 | TTC4 | 21.15 | 4.71 | 9.86 | 78.68 | 0.02515 |
| ENSG00000168916.11 | ZNF608 | 21.36 | 5.43 | 0.00 | 0.85 | 0.00165 |
| ENSG00000133812.10 | SBF2 | 21.42 | 45.34 | 39.90 | 6.14 | 0.0488 |
| ENSG00000106012.13 | IQCE | 21.84 | 55.60 | 3.61 | 47.81 | 0.0439 |
| ENSG00000139971.11 | C14orf37 | 22.26 | 9.61 | 1.15 | 50.49 | 0.0086 |
| ENSG00000138867.12 | GUCD1 | 22.36 | 48.68 | 10.17 | 224.51 | 0.04415 |
| ENSG00000267228.2 | IER3IP1 | 22.96 | 32.14 | 7.42 | 0.00 | 0.01955 |
| ENSG00000176390.10 | CRLF3 | 23.22 | 3.67 | 0.06 | 6.89 | 0.00585 |
| ENSG00000101290.9 | CDS2 | 23.78 | 0.94 | 51.41 | 3.45 | 0.03045 |
| ENSG00000165030.3 | NFIL3 | 23.84 | 32.66 | 30.14 | 219.23 | 0.0146 |
| ENSG00000198363.11 | ASPH | 23.84 | 230.74 | 326.46 | 97.56 | 0.019 |
| ENSG00000062650.13 | WAPAL | 24.14 | 56.28 | 9.24 | 121.79 | 0.02625 |
| ENSG00000172273.8 | HINFP | 24.42 | 16.38 | 0.06 | 0.26 | 0.04175 |
| ENSG00000224019.1 | RPL21P32 | 24.50 | 0.00 | 0.00 | 173.08 | 0.0054 |
| ENSG00000145194.13 | ECE2 | 24.63 | 33.05 | 0.18 | 16.46 | 0.04065 |
| ENSG00000141985.5 | SH3GL1 | 24.78 | 49.28 | 15.28 | 145.87 | 0.01315 |
| ENSG00000157895.7 | C12orf43 | 25.94 | 44.58 | 1.25 | 15.65 | 0.00735 |
| ENSG00000138663.4 | COPS4 | 26.31 | 22.05 | 31.53 | 202.21 | 0.0262 |
| ENSG00000169504.10 | CLIC4 | 26.70 | 140.30 | 205.12 | 48.45 | 0.01695 |
| ENSG00000132676.11 | DAP3 | 27.14 | 114.80 | 48.07 | 317.13 | 0.01545 |
| ENSG00000103275.14 | UBE2I | 28.48 | 34.42 | 17.49 | 91.88 | 0.0274 |
| ENSG00000122482.16 | ZNF644 | 28.54 | 18.23 | 27.17 | 3.57 | 0.04385 |
| ENSG00000127946.12 | HIP1 | 29.77 | 5.83 | 3.13 | 75.14 | 0.0379 |
| ENSG00000118260.10 | CREB1 | 31.96 | 4.70 | 42.52 | 3.49 | 0.0027 |
| ENSG00000152413.10 | HOMER1 | 32.53 | 4.81 | 1.83 | 90.78 | 0.00105 |
| ENSG00000090686.11 | USP48 | 33.75 | 118.84 | 39.13 | 133.69 | 0.0307 |
| ENSG00000075131.5 | TIPIN | 33.93 | 1.21 | 0.17 | 3.45 | 0.0392 |
| ENSG00000124574.10 | ABCC10 | 34.82 | 0.80 | 5.09 | 0.00 | 0.02555 |
| ENSG00000136153.15 | LMO7 | 35.40 | 384.16 | 247.03 | 1215.23 | 0.0112 |
| ENSG00000034677.7 | RNF19A | 37.93 | 22.98 | 13.14 | 163.02 | 0.03895 |
| ENSG00000063244.8 | U2AF2 | 38.77 | 3.04 | 15.08 | 1.20 | 0.043 |
| ENSG00000152942.14 | RAD17 | 39.05 | 6.99 | 5.55 | 158.97 | 0.0465 |
| ENSG00000113658.12 | SMAD5 | 39.06 | 60.62 | 18.06 | 251.89 | 0.04935 |
| ENSG00000066923.13 | STAG3 | 41.21 | 1.55 | 0.00 | 2.21 | 0.0047 |
| ENSG00000010318.15 | PHF7 | 44.31 | 5.43 | 0.00 | 3.88 | 0.012 |
| ENSG00000157500.6 | APPL1 | 44.31 | 62.47 | 47.78 | 4.28 | 0.01785 |
| ENSG00000144524.13 | COPS7B | 45.83 | 34.73 | 7.04 | 73.72 | 0.00975 |
| ENSG00000116679.11 | IVNS1ABP | 46.20 | 33.51 | 14.92 | 125.37 | 0.01845 |
| ENSG00000134363.7 | FST | 46.86 | 248.92 | 116.59 | 481.74 | 0.0361 |

TABLE 2-continued

List of the 386 genes differentially expressed in DiPS, DPSC, BDL-E5+, BDL-E5−

| Gene ID | Gene Symbol | DiPS | DPSC | BDL-E5+ | BDL-E5− | p value |
|---|---|---|---|---|---|---|
| ENSG00000168724.10 | DNAJC21 | 47.19 | 158.17 | 33.90 | 356.35 | 0.0107 |
| ENSG00000081320.6 | STK17B | 47.87 | 21.00 | 65.30 | 6.08 | 0.02835 |
| ENSG00000077782.15 | FGFR1 | 53.88 | 115.95 | 47.08 | 226.61 | 0.019 |
| ENSG00000131037.10 | EPS8L1 | 54.02 | 0.00 | 0.00 | 68.85 | 5.00E−05 |
| ENSG00000100796.13 | SMEK1 | 54.56 | 29.85 | 9.80 | 113.19 | 0.007 |
| ENSG00000112576.8 | CCND3 | 56.84 | 12.85 | 41.94 | 216.48 | 0.04555 |
| ENSG00000077312.4 | SNRPA | 57.78 | 5.97 | 3.16 | 100.41 | 0.0107 |
| ENSG00000038382.13 | TRIO | 58.79 | 62.20 | 10.88 | 116.43 | 0.0124 |
| ENSG00000117616.13 | C1orf63 | 59.63 | 357.82 | 133.16 | 732.99 | 0.0166 |
| ENSG00000112531.12 | QKI | 61.47 | 6.84 | 5.88 | 47.98 | 0.0346 |
| ENSG00000185864.12 | NPIPB4 | 61.65 | 24.39 | 3.66 | 36.08 | 0.0051 |
| ENSG00000140632.12 | GLYR1 | 62.41 | 25.16 | 3.82 | 127.73 | 9.00E−04 |
| ENSG00000064607.12 | SUGP2 | 66.35 | 40.94 | 18.89 | 2.14 | 0.03335 |
| ENSG00000163697.12 | APBB2 | 68.17 | 9.71 | 44.92 | 5.15 | 0.0026 |
| ENSG00000100836.6 | PABPN1 | 68.71 | 136.49 | 36.31 | 186.46 | 0.0399 |
| ENSG00000214021.11 | TTLL3 | 70.98 | 33.52 | 2.43 | 439.85 | 0.0016 |
| ENSG00000103091.10 | WDR59 | 76.24 | 8.34 | 2.46 | 55.56 | 0.04075 |
| ENSG00000242114.1 | MTFP1 | 76.61 | 0.00 | 1.52 | 147.89 | 0.0217 |
| ENSG00000116809.7 | ZBTB17 | 79.34 | 10.40 | 1.01 | 30.96 | 0.0256 |
| ENSG00000054654.11 | SYNE2 | 81.62 | 2.70 | 0.50 | 3.68 | 0.0446 |
| ENSG00000145016.9 | KIAA0226 | 89.15 | 11.86 | 9.78 | 139.03 | 0.0266 |
| ENSG00000109920.8 | FNBP4 | 92.79 | 42.91 | 33.64 | 230.39 | 0.0158 |
| ENSG00000119048.3 | UBE2B | 103.42 | 39.37 | 100.96 | 682.64 | 0.0443 |
| ENSG00000172889.11 | EGFL7 | 106.66 | 0.63 | 1.09 | 230.19 | 0.01655 |
| ENSG00000101115.8 | SALL4 | 106.90 | 5.55 | 0.00 | 74.06 | 5.00E−05 |
| ENSG00000089006.12 | SNX5 | 107.25 | 102.70 | 44.24 | 405.60 | 0.01565 |
| ENSG00000223745.3 | RP4-717123.3 | 108.07 | 11.50 | 55.98 | 5.28 | 0.029 |
| ENSG00000078808.12 | SDF4 | 111.39 | 113.08 | 19.25 | 419.99 | 0.0034 |
| ENSG00000150753.7 | CCT5 | 114.70 | 49.14 | 79.81 | 294.12 | 0.0456 |
| ENSG00000074054.13 | CLASP1 | 116.42 | 4.10 | 21.39 | 548.20 | 0.0067 |
| ENSG00000176022.3 | B3GALT6 | 121.05 | 36.08 | 29.74 | 238.61 | 0.0345 |
| ENSG00000118058.16 | KMT2A | 131.38 | 28.29 | 9.16 | 86.35 | 0.0133 |
| ENSG00000157110.11 | RBPMS | 135.68 | 51.42 | 17.47 | 188.47 | 0.01675 |
| ENSG00000114857.13 | NKTR | 137.91 | 92.83 | 23.91 | 169.09 | 0.0072 |
| ENSG00000197122.7 | SRC | 140.76 | 2.22 | 0.25 | 8.21 | 0.02595 |
| ENSG00000163714.13 | U2SURP | 151.90 | 162.07 | 42.15 | 384.12 | 0.0478 |
| ENSG00000184465.11 | WDR27 | 159.07 | 5.88 | 0.34 | 23.27 | 4.00E−04 |
| ENSG00000118420.12 | UBE3D | 164.38 | 2.03 | 3.43 | 0.00 | 0.01815 |
| ENSG00000078674.13 | PCM1 | 168.30 | 78.81 | 20.62 | 277.38 | 0.0087 |
| ENSG00000227540.1 | RP11-152N13.5 | 192.77 | 0.00 | 0.00 | 3.80 | 0.03325 |
| ENSG00000088448.10 | ANKRD10 | 203.31 | 220.78 | 22.86 | 349.50 | 0.00545 |
| ENSG00000167508.6 | MVD | 206.88 | 29.59 | 1.56 | 103.48 | 0.0225 |
| ENSG00000113013.8 | HSPA9 | 212.44 | 86.01 | 70.16 | 304.00 | 0.02625 |
| ENSG00000111215.7 | PRR4 | 216.81 | 153.65 | 62.96 | 0.91 | 0.0136 |
| ENSG00000101104.8 | PABPC1L | 217.65 | 0.20 | 6.83 | 140.08 | 0.04645 |
| ENSG00000108395.9 | TRIM37 | 221.03 | 46.46 | 9.74 | 142.01 | 0.00515 |
| ENSG00000129932.3 | DOHH | 231.87 | 3.48 | 0.74 | 0.00 | 0.0136 |
| ENSG00000091136.9 | LAMB1 | 235.00 | 123.61 | 46.18 | 317.48 | 0.0161 |
| ENSG00000168000.10 | BSCL2 | 262.44 | 172.02 | 41.28 | 475.11 | 0.0411 |
| ENSG00000103855.13 | CD276 | 263.15 | 70.14 | 43.84 | 307.87 | 0.0259 |
| ENSG00000076242.10 | MLH1 | 351.00 | 1.09 | 12.59 | 179.35 | 0.00955 |
| ENSG00000164292.8 | RHOBTB3 | 360.56 | 48.32 | 128.06 | 23.71 | 0.0216 |
| ENSG00000132589.11 | FLOT2 | 506.43 | 122.30 | 66.52 | 257.29 | 0.0479 |
| EN00000117523.11 | PRRC2C | 584.21 | 187.20 | 62.17 | 380.76 | 0.04055 |
| ENSG00000111642.10 | CHD4 | 826.30 | 694.96 | 78.30 | 1169.69 | 0.0155 |
| ENSG00000100401.15 | RANGAP1 | 896.77 | 106.57 | 36.05 | 257.91 | 0.03255 |
| ENSG00000141002.14 | TCF25 | 1709.60 | 676.19 | 229.02 | 1118.74 | 0.03775 |
| ENSG00000198804.2 | MT-CO1 | 2186.47 | 10593.20 | 1150.07 | 6626.71 | 0.0111 |
| ENSG00000101361.10 | NOP56 | 2251.98 | 158.79 | 31.64 | 220.42 | 0.04485 |
| ENSG00000214548.10 | MEG3 | 3738.76 | 600.30 | 96.15 | 384.80 | 0.02685 |

Example 8: CREB1 Affects Reprogramming Efficiency

Figure 7:
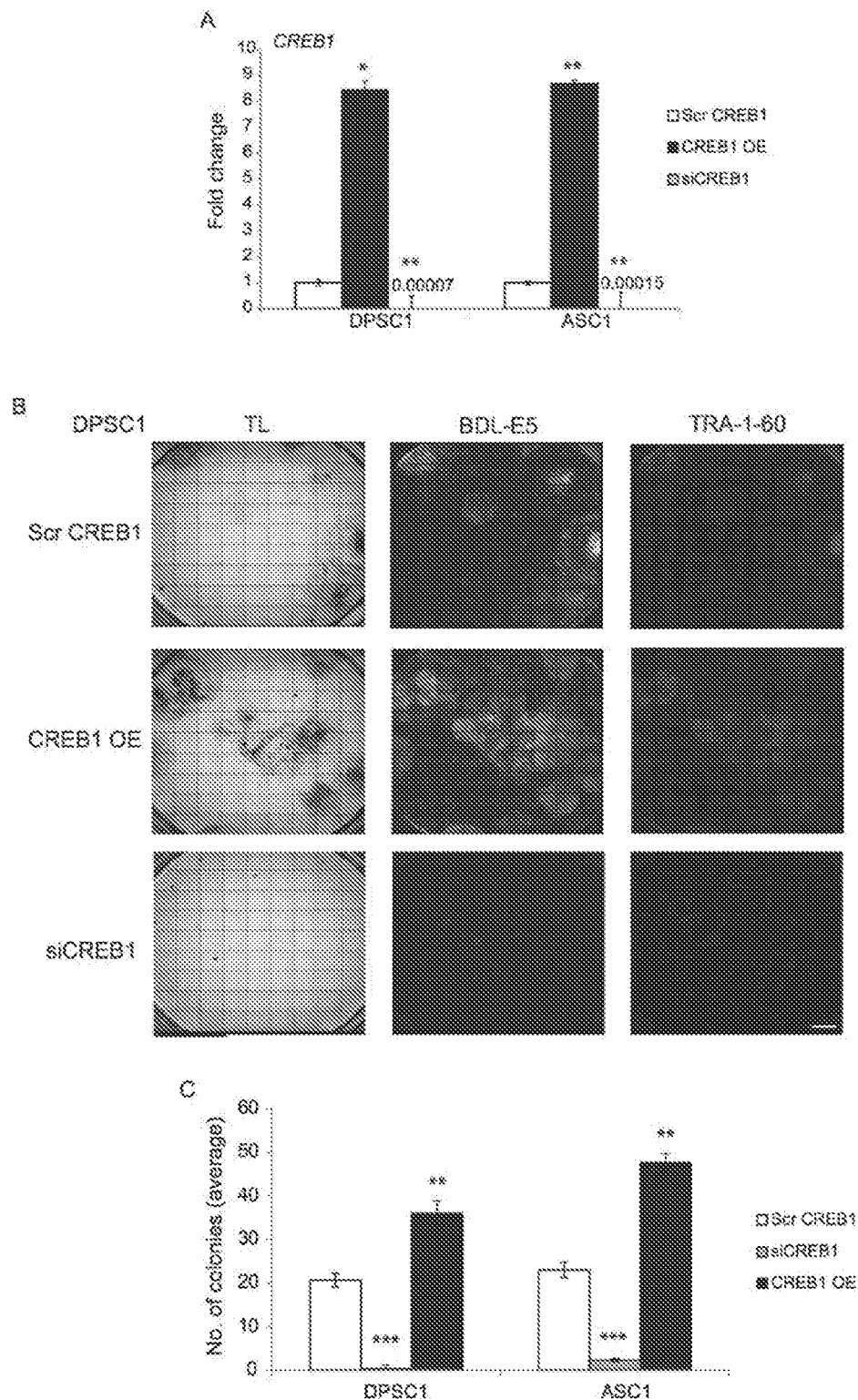
FIG. 7: (A) Graph showing mRNA expression of CREB1 in Scr CREB1, CREB1 OE and siCREB1 DPSC1 and ASC1 (n=3). *p<0.05 and p<0.01 denote significance compared with Scr DPSC1/ASC1. (B) TL and fluorescence images (10×) of BDL-E5, TRA-1-60 showing iPS colonies derived from DPSC1 transfected with Scr CREB1, CREB1 OE and siCREB1 at 12 dpn (n=3). Scale bar represents 100 µm. (C) Graph showing the average number of colonies in reprogrammed DPSC1 and ASC1 transfected with Scr CREB1, CREB1 OE, and siCREB1 at 12 dpn (n=3). p<0.01 and ***p<0.001 denote statistical significance.

In order to determine whether CREB1 plays a role in the reprogramming process and thus affects reprogramming efficiency, overexpression and knockdown of CREB1 was performed using CREB1 overexpression (CREB1 OE) vectors and siRNA targeting CREB1 (siCREB1), respectively. DPSC1 and ASC1 were either nucleofected with the CREB1 OE vectors or transfected with siCREB1 during reprogramming, then nucleofected with the episomal reprogramming factors. mRNA expression of CREB1 was significantly increased with CREB1 overexpression and significantly decreased with CREB1 knockdown in both DPSC and ASC lines (FIG. 7A). As shown in FIGS. 7B and 7C, overexpression of CREB1 increased the reprogramming efficiency in terms of the number of colonies and TRA-1-60-positive cells compared with the control (Scr CREB1) cells. Interestingly, knockdown of CREB1 drastically decreased the reprogramming efficiency and on average only <1 iPS colony per well was generated (FIGS. 7B and C). Knockdown and overexpression of CREB1 in ASCs also showed similar results. Knockdown of CREB1 significantly reduced the number of colonies and overexpression of CREB1 significantly increased the number of colonies formed (FIG. 7C). These results showed that CREB1 expression levels significantly influence reprogramming efficiency, indicating an important role of CREB1 in the reprogramming process into induced pluripotency.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

What is claimed is:

1. A labelled cell formed from a cell and a fluorescent compound of formula (I) or a pharmaceutically acceptable salt thereof

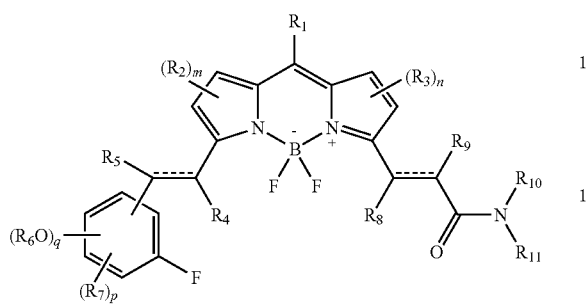

(I)

wherein:
$R_1$, $R_4$, $R_5$, $R_8$, $R_9$ and $R_{10}$ are each independently selected from the group consisting of H and methyl;
$R_2$, $R_3$, $R_6$ and $R_7$ are each methyl;
$R_{11}$ is $(CH_2)_2$—$N(CH_3)_2$;
m and n are each independently 0, 1, or 2;
p is 0, 1, 2, or 3,
q is 1, 2, 3, or 4, with the proviso that p+q≤4; and
--- means that the respective bond can be a single or double bond and, if it is a single bond, the additional valencies are hydrogen, and
wherein the cell is a cell undergoing reprogramming to become an induced pluripotent stem cell.

2. The labelled cell of claim 1, wherein the fluorescent compound is a compound of formula (II)

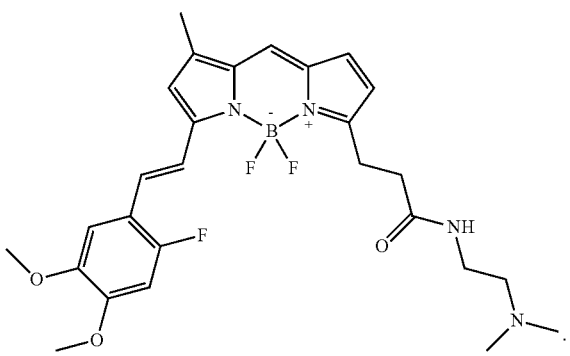

(II)

* * * * *